US012731689B2

(12) United States Patent
Charlap

(10) Patent No.: US 12,731,689 B2
(45) Date of Patent: Sep. 8, 2026

(54) MEDICAL DIAGNOSIS GENERATION

(71) Applicant: SOAP, Inc., Boca Raton, FL (US)

(72) Inventor: Steven Charlap, Boca Raton, FL (US)

(73) Assignee: SOAP, Inc., Boca Raton, FL (US)

( * ) Notice: Subject to any disclaimer, the term of this patent is extended or adjusted under 35 U.S.C. 154(b) by 175 days.

(21) Appl. No.: 18/525,115

(22) Filed: Nov. 30, 2023

(65) Prior Publication Data

US 2024/0355471 A1 Oct. 24, 2024

Related U.S. Application Data

(60) Provisional application No. 63/497,869, filed on Apr. 24, 2023.

(51) Int. Cl.

| | |
|---|---|
| ***G16H 50/20*** | (2018.01) |
| ***G16H 10/20*** | (2018.01) |
| ***G16H 20/10*** | (2018.01) |
| ***G16H 40/67*** | (2018.01) |
| ***G16H 50/30*** | (2018.01) |
| ***G16H 50/70*** | (2018.01) |

(52) U.S. Cl.

CPC ............ *G16H 50/20* (2018.01); *G16H 10/20* (2018.01); *G16H 20/10* (2018.01); *G16H 40/67* (2018.01); *G16H 50/30* (2018.01); *G16H 50/70* (2018.01)

(58) Field of Classification Search

CPC ...................................................... G16H 50/20

See application file for complete search history.

(56) References Cited

U.S. PATENT DOCUMENTS

| | | | |
|---|---|---|---|
| 7,877,272 B2 | 1/2011 | Rosales et al. | |
| 9,536,051 B1 | 1/2017 | Kabir | |
| 11,324,947 B2 | 5/2022 | Kaula et al. | |
| 11,404,170 B2 | 8/2022 | Charlap | |

(Continued)

FOREIGN PATENT DOCUMENTS

| | | | | |
|---|---|---|---|---|
| CN | 111415740 A | * | 7/2020 | ............ G06N 3/044 |
| CN | 113871003 B | | 4/2022 | |

(Continued)

OTHER PUBLICATIONS

Smith et al., Estimating the number of diseases—the concept of rare, ultra-rate, and hyper-rare, Aug. 19, 2022, iScience (Year: 2022).*

(Continued)

*Primary Examiner* — Karen A Hranek

(74) *Attorney, Agent, or Firm* — Merchant & Gould P.C.

(57) ABSTRACT

Leveraging generative artificial intelligence to provide diagnoses for patients. In some examples, elimination rules based on patient intake data are applied to a very large corpus of candidate diagnoses, such as all known human medical diagnoses, to narrow down the very large corpus of candidates to a meaningful differential diagnosis or final diagnosis. In some examples, targeted information is elicited to determine and apply additional elimination rules to further narrow down the candidate diagnoses. In some examples, patient intake data is classified into risk data and symptom data and processed by data type-specific machine learning models. In some examples, patient intake data is reconciled and correlated between risk and symptom data by specific machine-learning models to improve diagnostic clustering and accuracy.

17 Claims, 9 Drawing Sheets

(56) References Cited

U.S. PATENT DOCUMENTS

| | | | | |
|---|---|---|---|---|
| 11,587,678 | B2 | 2/2023 | Goetz et al. | |
| 2008/0177578 | A1 * | 7/2008 | Zakim | G16H 50/30 705/3 |
| 2009/0259494 | A1 * | 10/2009 | Feder | G06N 7/01 705/2 |
| 2018/0032864 | A1 * | 2/2018 | Graepel | G06N 3/08 |
| 2018/0068082 | A1 * | 3/2018 | Brown | G10L 15/08 |
| 2019/0108912 | A1 | 4/2019 | Spurlock, III et al. | |
| 2020/0265953 | A1 | 8/2020 | Corapi et al. | |
| 2021/0335491 | A1 * | 10/2021 | Morris | G06N 5/01 |
| 2022/0084677 | A1 | 3/2022 | Gupta et al. | |
| 2022/0215957 | A1 * | 7/2022 | Chen | G06N 3/0455 |
| 2022/0351858 | A1 | 11/2022 | Khan et al. | |
| 2023/0197225 | A1 * | 6/2023 | Lemme | G06V 40/10 434/262 |
| 2023/0215566 | A1 * | 7/2023 | Mahajan | G16H 40/67 705/2 |
| 2024/0177855 | A1 * | 5/2024 | Mishra | G16H 50/20 |
| 2024/0355484 | A1 * | 10/2024 | Garcia Santa | G16H 50/20 |
| 2025/0095642 | A1 * | 3/2025 | Ghose | G06N 7/01 |

FOREIGN PATENT DOCUMENTS

| | | | | |
|---|---|---|---|---|
| CN | 112164460 | B | 6/2023 | |
| JP | 2022074260 | A | 5/2022 | |
| JP | 2023025506 | A | 2/2023 | |
| WO | WO-2022069868 | A1 * | 4/2022 | G06N 5/01 |

OTHER PUBLICATIONS

Long; Large Language Model Guided Tree-of-Thought; May 15, 2023; arXiv.org (Year: 2023).*

Yao et al; Tree of Thoughts: Deliberate Problem Solving with Large Language Models; May 17, 2023; arXiv.org (Year: 2023).*

Ma et al.; Let's reward step by step: Step-Level reward model as the Navigators for Reasoning; Oct. 16, 2023; arXiv.org (Year: 2023).*

Richens et al., "Improving the accuracy of medical diagnosis with causal machine learning," Nature Communications, (2020)11:3923—https://doi.org/10.1038/s41467-020-17419-7—www.nature.com/naturecommunications (9 pages).

* cited by examiner

MEDICAL DIAGNOSIS GENERATION

CROSS-REFERENCE TO RELATED APPLICATIONS

This application claims the benefit of and priority to U.S. Provisional Application No. 63/497,869 filed Apr. 24, 2023, the contents of which are hereby incorporated by reference in their entirety. This application is related to U.S. patent application Ser. No. 15/490,780 filed Apr. 18, 2017 (now U.S. Pat. No. 11,404,170), the contents of which are hereby incorporated by reference in their entirety.

FIELD OF DISCLOSURE

The present disclosure is directed to improvements in earlier detecting and more accurately diagnosing human disease.

BACKGROUND

There are over 28,000 known human medical diagnoses. It is impossible for a medical professional to adequately consider each and every potentially relevant medical diagnosis when presented with a set of patient data. As a result, misdiagnosis of human disease is an unfortunately common occurrence in the medical profession. Misdiagnosis can occur, for example, when a diagnosis is made based on bias of the medical professional, incomplete information about the patient, irrelevant information about the patient, lack of knowledge of a medical professional, decision fatigue of a medical professional, a failure to properly weigh different pieces of patient information relative to one another, and/or assumptions about the patient that are incorrect.

SUMMARY

In general terms, the present disclosure is directed to improvements in early detection and speedier diagnosis of human disease.

In further general terms, one or more generative machine learning models is/are leveraged to obtain, consider and process an enormous amount of patient data, public data, and literature data and then map that data to a very large number of known human diagnoses by exclusion, elimination, mis-match and rule out rules to whittle down and single out the most accurate differential diagnosis and, in some examples, the most accurate final diagnosis than through conventional diagnostic methods.

In further general terms, the present disclosure is directed to leveraging generative artificial intelligence and/or machine learning to "octalating" a diagnosis to identify the final diagnosis based on eight key sources of "exclusion" data, the eight key sources including subjective patient data (e.g., subjective symptoms derived from a patient interview and shared personal and family medical history), objective patient data (e.g., biometrics, blood test results, imaging results, biopsy results, diagnostic procedure results, e.g. endoscopy, pulmonary function tests, and EKG, genetic testing results, molecular testing results, and physical examination), medical publications and texts that are analyzed and understood using one or more large language model(s) (LLM), social-ethnic-geographic-environmental-lifestyle-sexual-occupational-vaccination-physical trauma-temporal related risk factors data, childhood and adult mental health experiences and psychological and emotional state of the patient, population health data, subjective and objective response to treatment, and a corpus of all known human diagnoses. Examples herein describe how these eight primary sources of information can be accessed and used by one or more machine learning models to generate a differential diagnosis.

Systems and methods herein can be used to generate differential diagnoses as well as final diagnoses. Though some examples described herein may articulate that a differential diagnosis is achieved or achievable, it will be appreciated that those same examples can be applied to generate a final diagnosis. Similarly, though some examples described herein may articulate that a final diagnosis is achieved or achievable, it will be appreciated that those same examples can be applied to generate a differential diagnosis. As used herein a "final diagnosis" or, simply, "diagnosis" is a single medical diagnosis generated with a very high confidence (e.g., at least 75%, at least 80%, at least 85%, at least 90%, at least 95%, at least 96%, at least 97%, at least 98%, or at least 99% confidence). As used herein, a "differential diagnosis" can include multiple (two or more) candidate diagnoses, with equivalent and/or different confidence levels one from another, typically with each confidence level exceeding a predefined minimum threshold confidence (e.g., 10% or 15%). For example, a differential diagnosis could include Diagnosis A having a confidence level of 40%, Diagnosis B having a confidence level of 40%, and diagnosis C having a confidence level of 19%. Differential diagnoses will be described further herein.

According to certain aspects of the present disclosure, a computer-implemented method for generating a final diagnosis of a human disease of a patient, includes: receiving, with at least one machine learning model and via an input device, patient intake data related to the patient; accessing, with the at least one machine learning model and from at least one database, a collection of at least 7,000 up to all known candidate human medical diagnoses; determining, by the at least one machine learning model, a plurality of exclusion, elimination, mismatch, and rule-out rules based on the patient intake data; applying, by the at least one machine learning model, the plurality of exclusion, elimination, mismatch, and rule-out rules to the collection to whittle down and generate a sole medical diagnosis from among the collection; generating a differential diagnosis based on the subset, the differential diagnosis including medical diagnoses only from among the subset; and outputting the final diagnosis to an output device, the final diagnosis being selected from the medical diagnoses of the differential diagnosis.

According to further aspects of the present disclosure, a system for generating a diagnosis of a human disease of a patient, includes: one or more processors; and non-transitory computer-readable storage having stored thereon instructions which, when executed by the one or more processors, cause the one or more processors to: receive, with at least one machine learning model and via an input device, patient intake data related to the patient; access, with the at least one machine learning model and from at least one database, a collection of at least 7,000 up to all known candidate human medical diagnoses; determine, by the at least one machine learning model, a plurality of elimination rules based on the patient intake data; determine, by the at least one machine learning model, at least one by exclusion, elimination, mis-match and rule out rule based on the patient intake date; exclude, by the at least one machine learning model, one of the plurality of by exclusion, elimination, mis-match and rule out rules based on the at least one by exclusion, elimination, mis-match and rule out rules; determine, with the at least one machine learning model and based on the patient intake data, at least one question to pose to the patient or at least one test to administer to the patient; receive, with the at least one machine learning model, additional patient intake data based on at least one answer to the at least one question or at least one result of the at least one test; determine, by the at least one machine learning model, at least one additional by exclusion, elimination, mis-match and rule out rule based on the additional patient intake data; apply, by the at least one machine learning model, the additional by exclusion, elimination, mis-match and rule out rule and the plurality of by exclusion, elimination, mis-match and rule out rules except for the one of the plurality of exclusion, elimination, mis-match and rule out rules to the collection to generate a subset of candidate human medical diagnoses from among the collection; whittle down the differential diagnosis based on the subset, the differential diagnosis including medical diagnoses only from among the subset; and output the final diagnosis to an output device, the final diagnosis being selected from the medical diagnoses of the differential diagnosis.

According to further aspects of the present disclosure, a computer-implemented method for generating a final diagnosis of a human disease of a patient, includes: receiving, via an input device, patient intake data; determining that a first subset of the patient intake data relates to one or more physical symptoms of the patient; determining that a second subset of the patient intake data relates to a predisposition of the patient to each of a plurality of diseases independently of the one or more physical symptoms; providing the first subset of the patient intake data and the second subset of the patient intake data as inputs to a plurality of machine learning models, including: a risk model that receives, as risk input, the second subset of the patient intake data and generates, as risk output, the predisposition of the patient to the one or more diseases; and a diagnosis model that receives, as diagnosis input, the first subset of data and the risk output; generating, with the plurality of machine learning models, initially the differential diagnosis for the patient based on the first subset of the patient intake data and the second subset of the patient intake data; and outputting, by the diagnosis model, the final diagnosis to an output device.

According to further aspects of the present disclosure, a computer-implemented method for generating initially a differential diagnosis and then a final diagnosis of a human disease of a patient, includes: receiving, via an input device, patient intake data; determining that a first subset of the patient intake data relates to one or more subjective or objective physical symptoms of the patient; determining that a second subset of the patient intake data relates to a predisposition of the patient to each of a plurality of diseases independently of the one or more physical symptoms; providing the first subset of the patient intake data and the second subset of the patient intake data as inputs to a plurality of machine learning models, including: a risk model that receives, as risk input, the second subset of the patient intake data and generates, as risk output, the predisposition of the patient to the one or more diseases; and a diagnosis model that receives, as diagnosis input, the first subset of data and the risk output; accessing, with the diagnosis model and from at least one database, a collection of at least 7,000 up to all known candidate human medical diagnoses; determining, by the diagnosis model, a plurality of exclusion, elimination, mis-match and rule out rules based on the diagnosis input; applying, by the diagnosis model, the plurality of exclusion, elimination, mis-match and rule out rules to the collection to generate a subset of candidate human medical diagnoses from among the collection; generating the initial differential diagnosis based on the subset, the differential diagnosis including medical diagnoses only from among the subset; and outputting, by the diagnosis model, the final diagnosis to an output device, the final diagnosis being selected from the medical diagnoses of the differential diagnosis.

According to further aspects of the present disclosure, a computer-implemented method for generating a diagnosis of a human disease of a patient, includes: receiving, with at least one machine learning model and via an input device, patient intake data related to the patient; accessing, with the at least one machine learning model and from at least one database, a collection of at least 7,000 candidate human medical diagnoses; determining, by the at least one machine learning model, a plurality of elimination rules based on the patient intake data; applying, by the at least one machine learning model, the plurality of elimination rules to the collection to generate a subset of candidate human medical diagnoses from among the collection; generating the diagnosis based on the subset, the diagnosis including one of the medical diagnoses from among the subset; and outputting the diagnosis to an output device.

According to further aspects of the present disclosure, a system for generating a diagnosis of a human disease of a patient, including: one or more processors; and non-transitory computer-readable storage having stored thereon instructions which, when executed by the one or more processors, cause the one or more processors to: receive, with at least one machine learning model and via an input device, patient intake data related to the patient; access, with the at least one machine learning model and from at least one database, a collection of at least 7,000 candidate human medical diagnoses; determine, by the at least one machine learning model, a plurality of elimination rules based on the patient intake data; determine, by the at least one machine learning model, at least one inclusion rule based on the patient intake date; exclude, by the at least one machine learning model, one of the plurality of elimination rules based on the at least one inclusion rule; determine, with the at least one machine learning model and based on the patient intake data, at least one question to pose to the patient or at least one test to administer to the patient; receive, with the at least one machine learning model, additional patient intake data based on at least one answer to the at least one question or at least one result of the at least one test; determine, by the at least one machine learning model, at least one additional elimination rule based on the additional patient intake data; apply, by the at least one machine learning model, the additional elimination rule and the plurality of elimination rules except for the one of the plurality of elimination rules to the collection to generate a subset of candidate human medical diagnoses from among the collection; generate the diagnosis based on the subset, the diagnosis including one of the medical diagnoses from among the subset; and output the diagnosis to an output device.

According to further aspects of the present disclosure, computer-implemented method for generating a diagnosis of a human disease of a patient, includes: receiving, via an input device, patient intake data; determining that a first subset of the patient intake data relates to one or more physical symptoms of the patient; determining that a second subset of the patient intake data relates to a predisposition of the patient to each of a plurality of diseases independently of the one or more physical symptoms; providing the first subset of the patient intake data and the second subset of the patient intake data as inputs to a plurality of machine learning models, including: a risk model that receives, as risk input, the second subset of the patient intake data and generates, as risk output, the predisposition of the patient to the one or more diseases; and a diagnosis model that receives, as diagnosis input, the first subset of data and the risk output; generating, with the plurality of machine learning models, the diagnosis for the patient based on the first subset of the patient intake data and the second subset of the patient intake data; and outputting, by the diagnosis model, the diagnosis to an output device.

Computer-implemented methods described herein can be implemented as systems of one or more processors and non-transitory computer readable storage having instructions that perform various functions aligned with the computer-implemented methods. Likewise, systems disclosed here can be implemented as computer-implemented methods. In addition, computer-implemented methods and systems disclosed herein can be implemented as instructions stored on non-transitory computer readable storage.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures. Throughout the several figures, and wherever possible, like parts and features are indicated with like reference numbers.

DETAILED DESCRIPTION

Figure 1:
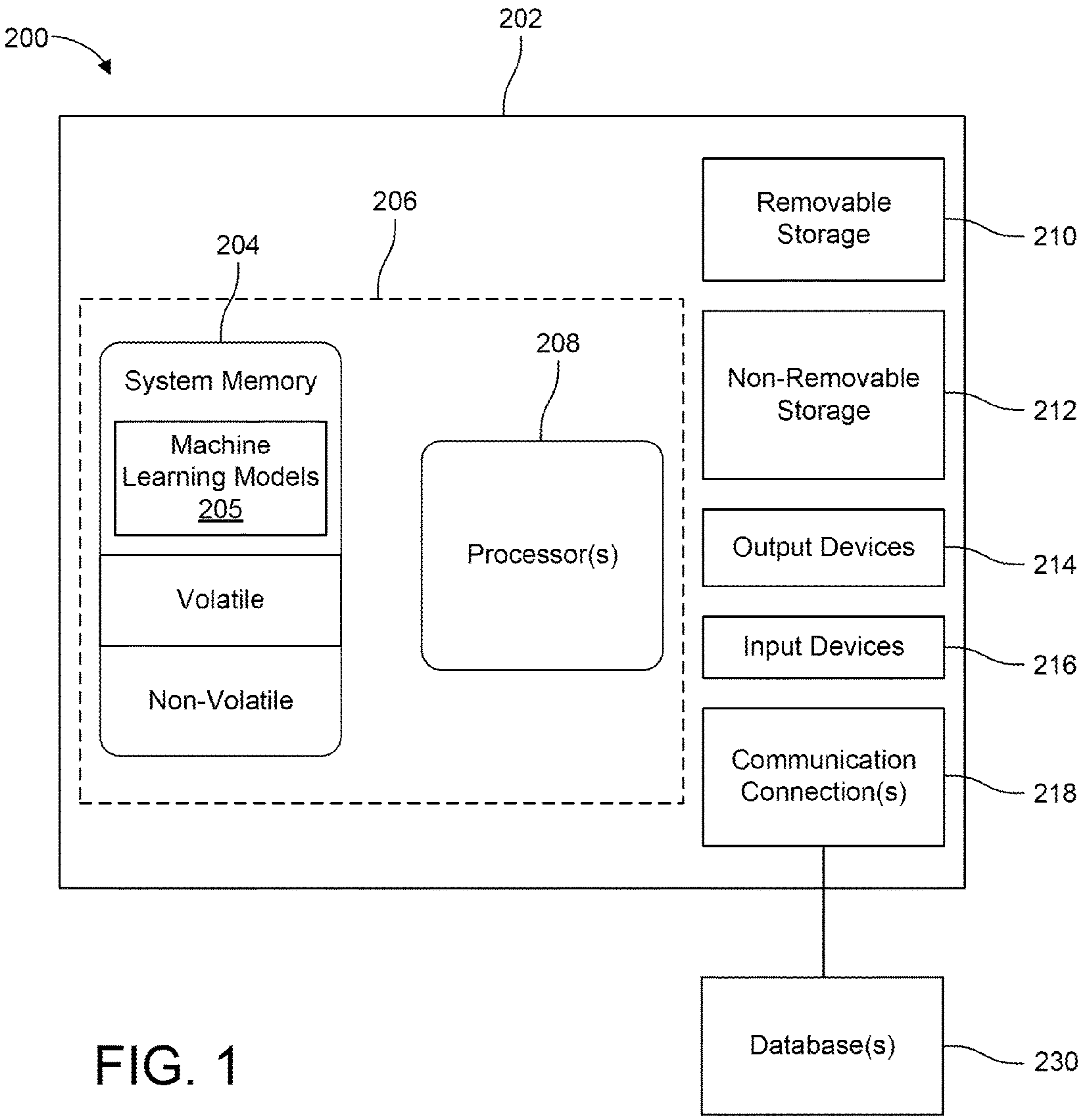
FIG. 1 schematically depicts an example system for generating a diagnosis in accordance with the present disclosure.

The present disclosure relates to improvements in human disease detection and diagnostics to reduce the chance of misdiagnosis and/or increase the chance of an earlier correct diagnosis. Correct, early diagnosis allows for early and proper treatment of the disease, which can dramatically increase the quality and/or length of life of the patient as compared with a later diagnosis and treatment regimen by which point the disease is more advanced, more difficult, more expensive, and more invasive to manage or cure.

There are more than 28,000 known medical diagnoses. Each diagnosis is associated with one or more patient-specific factors, such as physical symptoms, physical signs (e.g., absent bowel sounds, an enlarged lymph node, palpable liver, crackles on a lung exam, a heart murmur on a heart exam, leg edema), radiographic signs (e.g., x-ray, CT scan, Pet scan, MRI, EKG), blood levels (e.g., anemia, leukocytosis, polycythemia), hereditary risk factors, environmental risk factors, lifestyle risk factors, social determinants of health risk factors (e.g., food insecurity), preventive measure utilization risk factors, genetic risk factors, mental health risk factors, occupational risk factors, trauma and abuse risk factors, and the like. As one example of a social factor contributing to health problems, it has been found that patients with diabetes who cannot afford nutritious food (i.e., are considered to have food insecurity) are at more than twice the risk of severe hypoglycemia.

Typically, a medical professional (MP) employs a "rule in" methodology whereby, for example, based on one or more symptoms a patient is presenting, the MP identifies a number of candidate diagnoses referred to as a differential diagnosis.

A fundamental problem with this approach is that the MP cannot possibly consider all possible relevant diagnoses because there are simply too many and therefore may never even consider the right diagnosis.

Another fundamental problem with the typical approach to medical diagnostics is that medication side effects and contraindications are disregarded or not adequately considered as potential causes for symptoms and/or disease.

Another fundamental problem with the typical approach to medical diagnostics is that can be impossible to consider and appreciate all factors relevant to the correct diagnosis. Key factors can be overlooked and/or irrelevant factors can be given too much weight.

Another fundamental problem with the typical approach to medical diagnostics is the failure to identify or fully consider present risk factors; failure to order additional testing; and failure to generate an extensive enough differential diagnosis. Time-constrained, knowledge-limited, decision-fatigued, cognitively-biased and administratively burdened MPs are often incapable of consistently avoiding misdiagnosis errors leading to, for every 100 physicians there being 97 malpractice suits, and according to the American Medical Association, 65% of physicians reporting a malpractice suit having been filed against them by age 55. According to a recent John Hopkins University study, misdiagnosis happens on average every 2.6 seconds, a death or permanent disability happens on average secondary to misdiagnosis every 40 seconds, resulting in about 800,000 people dying or developing permanent disabilities each year from misdiagnosis. The problem is so far reaching that the National Academy of Medicine now predicts that everyone will experience a diagnostic error during their lifetime.

As just one of many examples of underperforming medical diagnostics, many of the major causes of human morbidity and mortality, such as heart diseases, cancers, type 2 diabetes, stroke, and life-threatening infections often initially present with relatively benign symptoms that can easily be mistaken for other less harmful and concerning conditions, leading to missed early diagnoses. In fact, most medical students are taught that "when you hear hoofbeats, think of horses not zebras." This is an admonishment to first focus on the most common diagnosis. This common teaching results in physicians often overlooking less common but more serious diagnoses at first. For example, a patient presenting with a sore throat can have different etiologies for the soreness. The throat could be sore due to a common virus, which typically does not require treatment other than palliative care and will usually resolve on its own. The sore throat could be bacterial and require a throat culture to confirm diagnosis. If the culture identifies a bacterial cause such as *streptococcus*, typically antibiotic treatment is indicated and prescribed to hasten recovery and avoid rheumatic heart disease. A sore throat can also be associated with infectious mononucleosis, which requires a monospot test to identify. If the test confirms mononucleosis, then strict bedrest to avoid splenic rupture, and contagion, to avoid spread, are indicated. A sore throat can also be associated with both leukemia and lymphoma, both life-threatening cancers, which require an initial complete blood count to increase suspicion. Delays in diagnosis can lead to permanent disabilities from more invasive treatments, greater costs, pain and suffering, and fatalities. Also, many MPS many never experience an uncommon or rare disease and may not remember or recognize the disease thereby again missing altogether or delaying the right diagnosis.

A common thread among these failures and inefficiencies of conventional medical diagnostics is that the MP cannot possibly appreciate or be aware of all, of the potentially relevant pieces of information when making a diagnosis, or how those pieces of information interrelate or interact, particularly when subjected to time-constraints, knowledge-limits, decision-fatigue, cognitive-bias and administrative burdens. The relevant pieces of information include all possible diagnoses, the corpus of medical diagnostic publications and texts, and all patient-specific subjective and objective factors, as well as community factors, that may impact what diagnoses may be relevant or not relevant. Moreover, not only can patient-specific factors, as well as community factors, independently impact what diagnoses may be relevant, more relevant, or not relevant, patient-specific and community (e.g., public health) factors may also be relevant to diagnoses only, or more so, in combination with one or more other patient-specific factors. For example, a patient's race considered on its own may be of limited diagnostic relevance, and a patient's gender considered on its own may be of limited diagnostic relevance, but the patient's race and gender within a certain geographically located community may be significant based on prevalence of disease within the community. The complexity of the interactions and effects of all of the patient-specific and community factors is enormous and beyond the abilities of any MP. As a result, the differential diagnosis is often underinclusive and overinclusive, failing to identify or adequately weight relevant diagnoses, and identifying or attributing too much weight to irrelevant common diagnoses, which can have catastrophic consequences (e.g., overlooking a treatable life-threatening diagnosis, prescribing a treatment that does not help the patient, delaying treatment, or that harms the patient, failing to deprescribe a medication or treatment that is harming the patient, etc.).

As one of innumerable examples of the pitfalls in conventional medical diagnostics, a 35-year-old patient who presents with sudden onset stomach pain and indigestion unrelated to food ingestion would most commonly be thought to have gastroenteritis. However, knowledge of early colon cancer in the family would raise the relevance of considering colon cancer as part of the diagnosis. Likewise, collection and consideration of the absence of such a history, would reduce suspicion of a hereditary mediated diagnosis.

As another example, a young patient presents with fainting while playing basketball. A family history of Sudden Infant Death Syndrome (SIDS) or drowning accident should increase suspicion of cardiac myopathy or short QT syndrome because both deaths can be due to underlying heart disease. Lack of any related heart disease history should significantly reduce suspicion and suggest other avenues of exploration.

As another example, social determinants of health such as lack of consistent access to food due to lack of funds should increase suspicion of a nutritional deficiency in a patient complaining of headaches.

As another example, identifying that a patient is taking a medication that routinely and commonly causes heartburn should lead to identification of the cause if in fact the presenting symptom of heartburn is being caused by the medication.

As another example, unsuccessfully treating a suspected condition with a known highly effective treatment can serve to eliminate the diagnosis.

As another example, knowing that a patient had his spleen removed can eliminate diagnoses associated with the spleen.

As another example, identifying that a patient's blood test reveals absence of Rheumatoid Factor can eliminate rheumatoid arthritis as a diagnosis.

In general terms, the present disclosure is directed to using generative artificial intelligence to improve early and correct diagnosis of human disease.

Machine learning models process very large numbers of patient-specific and community factors against all possible medical diagnoses and other data available, such as medication specifications, side effects, and contraindications to arrive at more reliable differential diagnosis. Aspects of the present disclosure relate to novel and technologically centered methods and systems for diagnosing disease or another medical issue in a patient, leveraging generative artificial intelligence to generate diagnoses that were heretofore impossible due to piecemeal, under-informed, and misguided approaches to medical diagnosis. The result is a far more comprehensive and accurate understanding of the individual patient's condition, reflecting a desperately needed improvement in medical diagnostics and healthcare more generally.

According to a first aspect of the present technology, generative artificial intelligence (AI) is used to employ a "rule out" methodology, whereby a machine learning model is provided with subjective and objective patient data and, beginning from the entire corpus (e.g., a database) of (28, 000 plus) possible diagnoses applies rules of elimination, exclusion, and mis-match based on the subjective and objective patient data, community data, and the corpus of medical publications and texts to arrive at all possibly applicable candidate diagnoses, from which the model then generates a final diagnosis. The elimination rules are applied according to the patient data factors, such as age, gender, race, normal and abnormal blood results, urine results, genetic test results, absent and present radiographic findings, absent and present findings from other studies, normal and abnormal ultrasounds, biopsy results, absent and present physical findings, absent and present symptoms, absent and present personal medical history, absent and present history of exposures, absent and present history of traumas, absent and present history of pregnancy, extensive up to three generation (or more) family history, normal and abnormal EKG results, normal and abnormal EEG results, a negative or positive peripheral smear, a negative or positive culture, absence or presence of abnormal mental health history, social determinants of health, absence or presence occupational exposures, absence or presence environmental exposures, absence or presence geographic related diseases, and the like.

According to a second aspect of the present technology, a machine learning model generates a differential diagnosis by, in part, considering as inputs both patient data (e.g., symptoms, physical signs, risk factors, medications, etc.) and medication side effects and contraindications relevant to any medications the patient is taking or has taken within a relevant time period to rule out irrelevant diagnoses. The medication side effects data can be obtained from a database that stores all side effects of all medications, their likelihoods, including proclivities for side effects based on age, gender, pharmacogenetics, and race, and the patient data factors (e.g., family history, personal medical history, exposures, other medical conditions) that increase or decrease their likelihood. The machine learning model reconciles the medication side effects data against the patient factor data as part of generating a differential diagnosis based on eliminating not relevant or possible diagnoses.

According to a third aspect of the present technology, one or more machine learning models can be employed to perform, in sequence and for a given patient, a risk assessment followed by symptom and physical finding/sign assessment to generate a differential diagnosis. For example, a machine learning model parses patient intake data into multiple subsets of patient data as follows. One subset of patient data can relate to the patient's physical symptoms. Another subset can relate to the patient's predispositions to various diseases independently of any physical symptoms. Another subset can relate to patient data factors that are relevant to medications the patient is taking or has taken recently and whether the patient may be experiencing side effects of those medications. The machine learning model processes each subset of data both separately and collectively in order to generate a differential diagnosis for the patient by both identifying relevant diagnoses and eliminating irrelevant diagnoses.

According to a fourth aspect of the present technology, one or more machine learning models can be employed to perform, in sequence and for a given patient, a generative AI assessment of a differential diagnosis to determine which additional objective patient data factors would narrow the diagnosis list by making specific recommendations for the MP for collection of objective patient data such as blood tests, genetic tests, scans, biometrics, biopsies, etc. to further narrow the diagnosis list even before the patient presents for the medical encounter.

According to a fifth aspect of the present technology, one or more machine learning models can be employed to perform, in sequence and for a given patient, a generative AI assessment of an initial comprehensive medical intake, which includes collection of a chief complaint, history of present illness, denied symptoms, past medical and surgical history, family medical history, social determinants of health, mental health, lifestyle, medications and allergies, occupational and environmental exposures, etc., whether performed by a conversational and generative AI model, an MP, or another interviewer, to determine based on medical publications, texts, common knowledge, or experience, which additional medical questions, queries, and follow-on questions, should be asked of the patient to ensure the completeness of the medical history intake to arrive at the most accurate diagnosis.

Further aspects of the present disclosure relate to any combination of the foregoing aspects.

FIG. 1 schematically shows an example system 200 for generating a diagnosis in accordance with the present disclosure.

The system 200 includes a computing device 202. The computing device 202 may be a server and/or other computing device that performs the operations discussed herein, such as processing of all patient-specific factors (e.g., risk factor data, symptom data, medication data, physical sign data, demographics data, social data, etc.), processing of all known medical diagnoses, processing of non-patient specific medication data (e.g., side effects, contraindications), and generating a diagnosis based on that data.

The number of known medical diagnoses initially considered by the computing device according to embodiments of the present disclosure vastly outnumbers the physical and mental capabilities of a medical professional or even a large team of medical professionals. In some examples, at least 7,000 known medical diagnoses are initially processed by the computing device 202 to arrive at a differential diagnosis and/or a final diagnosis according to embodiments described herein. In some examples, at least 10,000 known medical diagnoses are initially processed by the computing device 202 to arrive at a differential diagnosis and/or a final diagnosis according to embodiments described herein. In some examples, at least 15,000 known medical diagnoses are initially processed by the computing device 202 to arrive at a differential diagnosis and/or a final diagnosis according to embodiments described herein. In some examples, at least 20,000 known medical diagnoses are initially processed by the computing device 202 to arrive at a differential diagnosis and/or a final diagnosis according to embodiments described herein. In some examples, at least 25,000 known medical diagnoses are initially processed by the computing device 202 to arrive at a differential diagnosis and/or a final diagnosis according to embodiments described herein. In some examples, at least 28,000 known medical diagnoses are initially processed by the computing device 202 to arrive at a differential diagnosis and/or a final diagnosis according to embodiments described herein. As medical science develops and more diagnoses are identified, the number of diagnoses considered can likewise increase.

The computing device 202 may include computing components 206. The computing components 206 include at least one processor 208 and memory 204. The memory 204 can include a non-transient (non-transitory) computer-readable medium. Depending on the exact configuration, the memory 204 (storing, among other things, generative machine learning models 205 such as a risk model and a diagnosis model and includes instructions to perform other operations disclosed herein) can be volatile (such as RAM), non-volatile (such as ROM, flash memory, etc.), or some combination of the two. The memory 204 can store different software modules to perform operations disclosed herein for receiving and processing data, such as a speech-to-text module, a text-to-speech model, natural language understanding modules, dialog management modules, and modules configured to generate audible responses to patients' verbalized data.

The computing device 202 may also include storage devices (removable 210, and/or non-removable 212) including, but not limited to, solid-state devices, magnetic or optical disks, or tape.

The computing device 202 may also have input device(s) 216 such as touch screens, keyboard, mouse, pen, voice input (e.g., microphone), visual camera, thermometer, pulse meter, oximeter, blood pressure meter, etc.

The computing device 202 may have one or more output device(s) 214 such as a display, speakers, printer, etc.

One or more communication connections 218, such as local-area network (LAN), wide-area network (WAN), point-to-point, Bluetooth, RF, etc., may also be incorporated into the computing device 202 to enable communication between components of the system 200 and other systems and/or to enable communication between components of the system 200 itself.

Via the communications connections 218, the computing device 202 can access database(s) 230 of the system 200. One or more of the database(s) 230 can be managed externally by third parties. The database(s) 230 can be publicly accessible and/or require a subscription or permission to obtain access. The database(s) 230 store information that can be used by the machine learning models 205, together with patient specific factors data, to generate a differential diagnosis and/or a final diagnosis for the patient. The databases 230 can also include repositories of network-accessible information that can be used to generate a differential diagnosis and/or a final diagnosis, such as websites that include social-ethnic-geographic-environmental data, such as census data municipal data. Based on, e.g., the patient's address, relevant pieces of such data can then be associated with the patient, with a family of the patient, or with a residential address of the patient, and used in the process of generating a differential diagnosis and/or a final diagnosis for the patient. In some examples, the computing device 202 includes a web crawling device configured to pull data from websites (e.g., municipal data) and supply it to the machine learning models 205.

The machine learning models 205 develop and apply algorithms that map patient-specific factors and other data (e.g., non-patient specific data about medications) to candidate diagnoses using hyperparameters for each patient-specific factor and calculate likelihoods for different diagnoses. The machine learning models 205 can continuously retune the hyperparameters as more data is fed into the system, resulting in increasingly reliable differential diagnosis and final diagnosis outputs. For example, a given algorithm can include at least 10, 100, 1,000, 10,000 or more present or non-present patient specific and—non patient specific factors each weighted according to its own hyperparameter tuned to minimize an error function associated with a diagnostic prediction generated by the algorithm. The hyperparameters can be independent or dependent on others. For example, if a certain two patient specific factors are present, they can each be weighted more than if only one of those factors were present. As another example, if two patient specific factors are not present, their non-presence is factored in the algorithm, whereas if only one of them is not present then the non-presence of the other is not factored in the algorithm.

Components of the system 200 may be integrated at one location, or distributed across a network with the different components being networked together via, e.g., the Internet and/or one or more of the networking schemes just described. For instance, the machine learning models can be built, stored and run on a remote server (e.g., a Cloud server), while the input device and output devices are local to the patient or clinician.

The machine learning models 205 can be constructed according to any type of machine learning technique suitable to generate the differential diagnosis and/or final diagnosis based on the described inputs, such as supervised learning, unsupervised learning or semi-supervised learning. Machine learning (ML) can be generally defined as the field of artificial intelligence (AI) that provides computers with the ability to learn without being explicitly programmed. Machine learning focuses on the development of computer programs that can teach themselves to grow and change when exposed to new data. In other words, machine learning can be defined as the subfield of computer science that "gives computers the ability to learn without being explicitly programmed." Machine learning explores the study and construction of algorithms that can learn from and make predictions on data-such algorithms overcome following strictly static program instructions by making data-driven predictions or decisions, through building a model from sample inputs. For example, a machine learning model for diagnosis prediction can be composed of one or more artificial neural networks (ANN), which is a type of machine learning designated to learn and recognize patterns in data. ANNs typically consist of multiple layers of processing nodes (or neurons) densely connected, where an input signal (or data) moves through the input to the output layer. As a signal crosses the processing nodes on each layer, it is transformed and propagated to the next layer, until all the transformed signals are combined in the output layer to compose the model's output (or prediction). The ANN may have suitable architecture and/or configuration that varies according to the task it was designed to address. Convolutional Neural Networks (CNN), Feedforward Neural Networks (FNN), and Recurrent Neural Networks (RNN) are well-known examples of different types of ANN. In some embodiments, the neural networks may also be configured in a "deep" setting (also known as deep learning), having tens of layers and millions or even billions of parameters. That allows the ML model to deal with large amounts of data. In examples of diagnosis prediction, there may be two sets of neurons: ones that receive an input signal (e.g., an input signal corresponding to the patient input data described herein) and ones that send an output signal (e.g., a signal representing a differential diagnosis as described herein). When the input layer receives an input, it passes on a transformed version of the input to the next layer. In a base model, there are many layers (often called hidden layers) between the input and output, allowing the algorithm to use multiple processing layers, composed of multiple linear and non-linear transformations.

The machine learning models 205 can include one or more Process Reward Models (PRM). A PRM is configured to intricately assess and scoring each step of the machine learning diagnosis elimination process as described herein, enabling more accurate decision-making over time by more precise elimination and assessment of diagnosis outputs, particularly in complex scenarios such as identifying rare, hard to diagnose conditions. The machine learning models 205 can combine a PRM with a Tree of Thoughts (TOT) method of reasoning, allowing a generative AI machine learning reinforcement model 205 to navigate through a myriad of reasoning steps by constantly adjusting its route through the branches of the tree based on both prior conclusions and future assertions before arriving at a differential diagnosis and/or a final diagnosis by ensuring it processes and prioritizes the most relevant of the input information to achieve the shortest possible path to determining the final diagnosis. That is, over time, the machine learning model 205 learns to optimize the shortest possible path through the TOT from the input information for a given patient at the top of the tree (e.g., the eight primary sources of information described herein) to the final diagnosis for that patient.

An example TOT model optimization process will now be described. All types of information necessary to create a set of rules that define the different diagnoses is consumed. Such information can include, for example, subjective patient data (e.g., subjective symptoms derived from a patient interview and shared personal and family medical history), objective patient data: (e.g., biometrics, blood test results, imaging results, biopsy results, diagnostic procedure results (e.g. endoscopy, pulmonary function tests, and EKG, genetic testing results, molecular testing results, and physical examination)), medical publications and texts that are analyzed and understood using one or more large language model(s) (LLM), social-ethnic-geographic-environmental-lifestyle-sexual-physical trauma-temporal-occupational related risk factors data, childhood and adult mental health experiences and psychological and emotional state of the patient, population health data, subjective and objective response to treatment, and a corpus of all known human diagnoses.

The raw data just described is transformed into a corresponding set of diagnosis rules by the rule generator component by performing the following steps. First, the raw data is collected from the different sources of information and stored in a centralized repository. It is in this step that the types of data (structured or unstructured) present in each data source are identified and mapped into qualitative and quantitative types. Next all the unnecessary, incorrect, corrupted, incorrectly formatted, duplicated, or incomplete data obtained mainly from the process of merging the data from different sources are corrected for, thereby "cleaning" the raw data. Next, the raw data is converted from one format into another format. In particular, the cleaned raw data is transformed into a standardized format that can be processed further by the rule generator component. This process also involves the transformation of unstructured data into structured data. For example, an unstructured data object having the raw data "A 39-year-old male patient complains of severe headaches" is transformed to a structured data object having the form of a table. The table has a column of factors, with a row for age, a row for gender, a row for symptom, and a row for symptom severity, and a second column having a value for each factor. For example, the second column includes 39 for age, male for gender, headache for symptom, and severe for symptom severity. Next, the cleaned, standardized, and transformed data is analyze and summarized to find relevant patterns, trends, and insights. From the statistics generated it is possible to detect outliers and statistically non-significant correlations. Next, the dataset used to train the machine learning model is defined based on the findings of the previous step. The dataset is presented in tabular form and represents a mapping between input(s) and output(s) variables, as in the example table below, where the hypothetical dataset is composed of four input variables and one output variable, and each row represents an instance of data:

| Input 1: Age | Input 2: Gender | Input 3: Symptom | Input 4: Severity | Output: Diagnosis Name |
|---|---|---|---|---|
| 39 | Male | Headache | Severe | Diagnosis 1 |
| 20 | Female | Back-Pain | Mild | Diagnosis 2 |

Next, rule-based machine learning methods are applied to the dataset to learn relationships that represent matching criteria for each existing diagnosis in the form of IF-THEN rules. This process is repeated until some acceptance criterion based on the model's performance is achieved. In case of acceptance, a resulting set of diagnosis rules is generated. Otherwise, this training process is repeated and may undergo adjustments in the dataset construction steps.

The resulting diagnosis rules can be seen as an extensive knowledge base describing the logical conditions that represent each candidate diagnosis. However, even with such a set of rules, it may still be not possible to identify the patient's diagnosis because, in most cases, the patient's available data does not have all the information (such as blood test results, image test results, biopsy results, etc.) necessary to verify the matching criteria of all possible diagnoses in the rule set. In this case, a mechanism is needed to optimally rule out potential diagnoses, avoiding unnecessary information requests to conduct the final diagnosis. The mechanism receives as input both the patient-specific data (e.g., the entire medical history, lab tests, symptoms, lifestyle factors, etc.) and the set of diagnosis rules that describe the candidate diagnoses. The decision-making process is defined by a reinforcement learning-based approach that iterates over the knowledge base composed of the existing rule set and set of patient information to learn the optimal set of actions, such as information requests, test requests, etc. that should be taken to reach a final diagnosis state.

The process of choosing an action (e.g. request MRI scan), performing an action (e.g. request the patient to execute an MRI scan), measuring the quality or reward of an action (e.g. identify whether the result was relevant to test a diagnostic hypothesis, and updating the knowledge base is repeated over and over until an output diagnosis state is reached (in case of success) or an algorithm stopping criteria is reached, when the algorithm fails to converge to an optimal solution (or diagnosis). In the latter case, a set of new actionable insights based on user information and the set of rules are returned in the form of research questions that must be addressed by the literature and feed back into the model. At the end of this process, an optimal policy, capable of mapping states (patient data and rule set) to actions (request information/tests/etc.) is generated.

Figure 2:
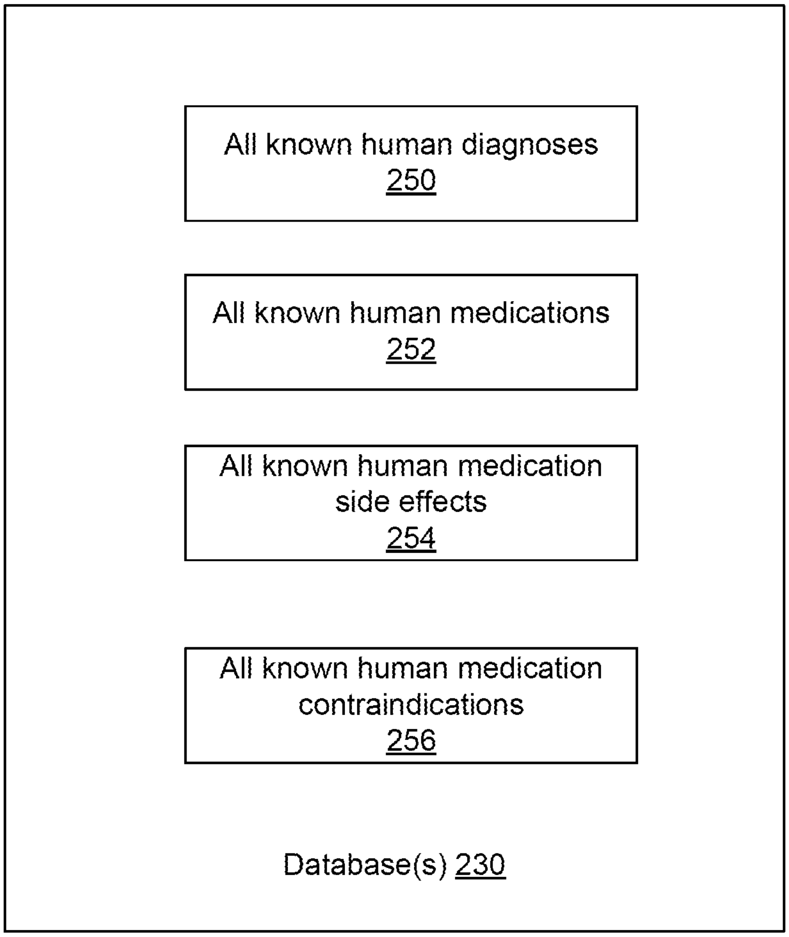
FIG. 2 depicts a portion of the system of FIG. 1 in greater detail.

FIG. 2 depicts a portion of the system of FIG. 1 in greater detail. In particular, FIG. 2 depicts example data stored by the database(s) 230.

The information stored by the databases(s) 230 can include, for example, all known human diagnoses 250 (e.g., more than 28,000 diagnoses that increase in number as medical science progresses), all known human medications 252, all known human medication side effects 254 mapped to their respective medications, their likelihood and rate of occurrence based on the presence of other patient factors, etc., and all known human medication contraindications 256 mapped to their respective medications, their likelihood and rate of occurrence based on the presence of other patient factors, etc. The machine learning models 205 are configured to access the information 250, 252, 254, 256 and process that information together with patient-specific information to generate a differential diagnosis for the patient.

Figure 3:
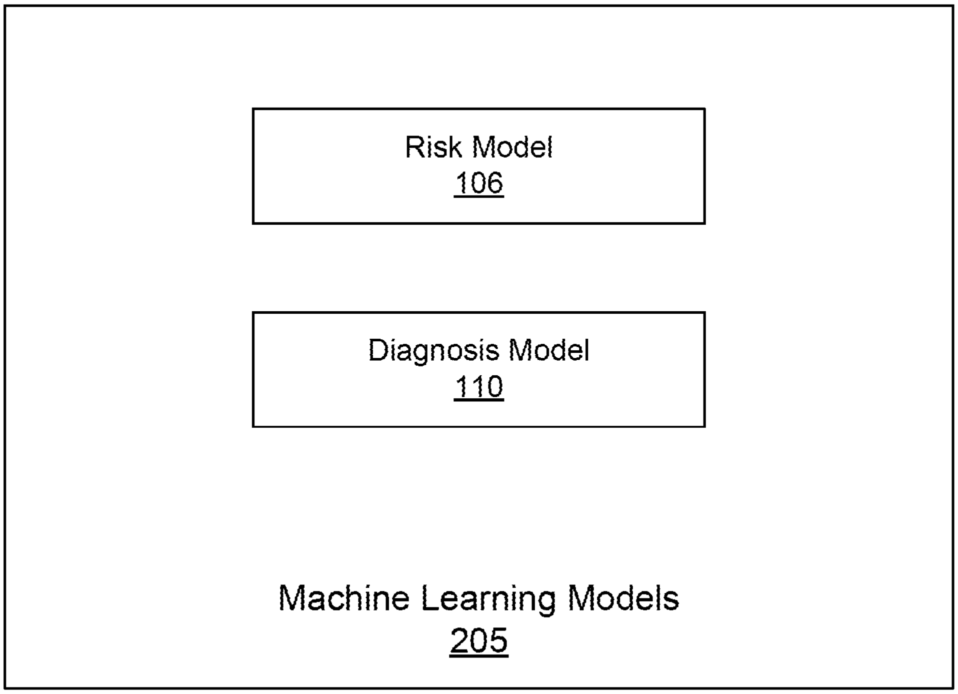
FIG. 3 depicts a further portion of the system of FIG. 1 in greater detail.

FIG. 3 depicts a further portion of the system of FIG. 1 in greater detail. In particular, FIG. 3 depicts example machine learning models 205. For example, the machine learning models 205 can include a risk model 106 and diagnosis model 110. These models will be described in greater detail below.

Figure 4:
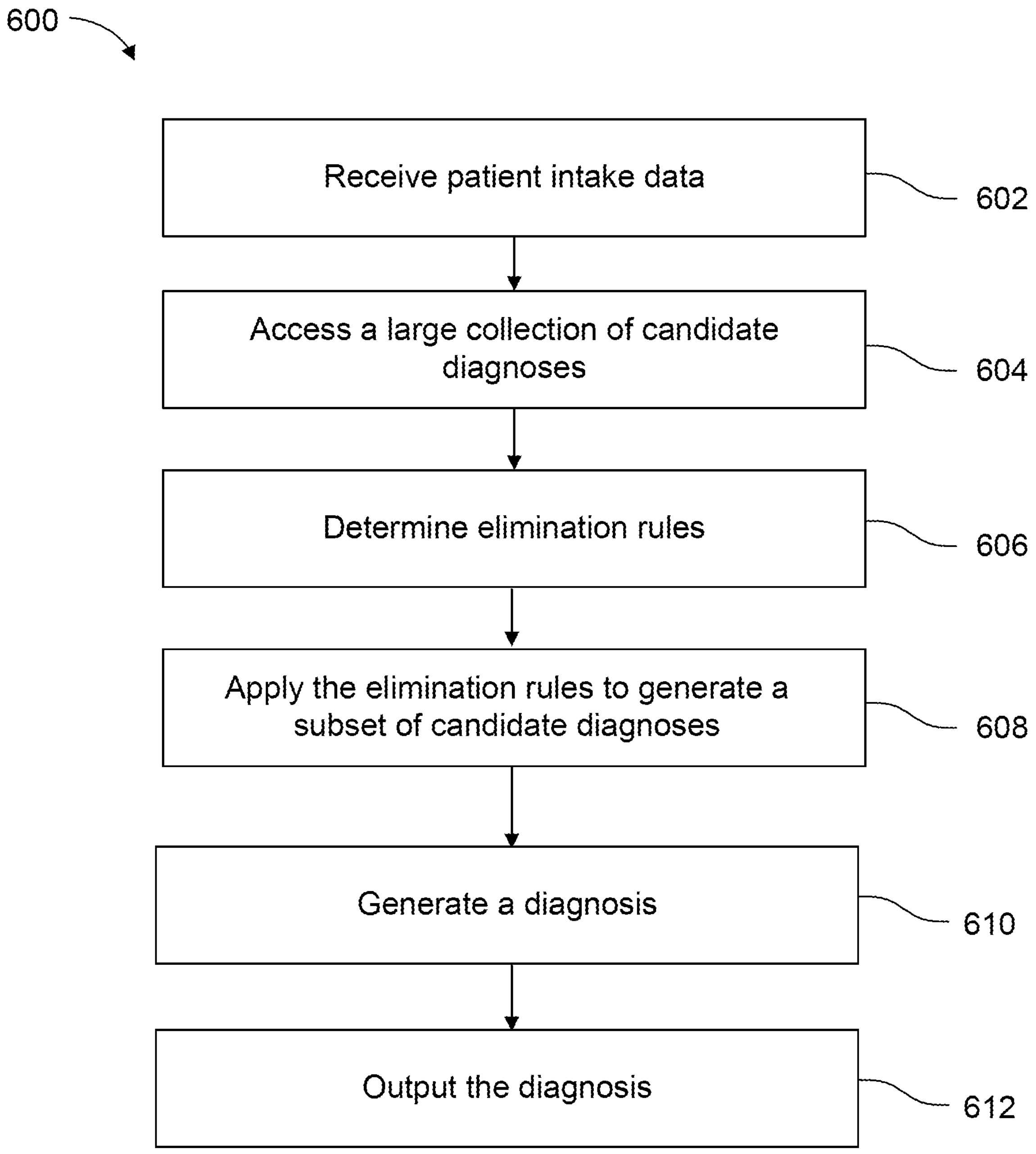
FIG. 4 depicts an example method of generating a diagnosis in accordance with the present disclosure.

FIG. 4 shows an example method 600 of generating a diagnosis in accordance with the present disclosure. The method 600 embodies various methods according to the present disclosure that include subsets of the depicted steps.

In some examples, the steps of the method 600 can be performed by the computing device 202. In some examples, the steps of the method 600 can be performed by the machine learning models 205. In some examples, the steps of the method 600 can be performed by the risk model 106 and the diagnosis model 110. In some examples, the steps of the method 600 can be performed by the diagnosis model 110 alone. For purposes of the following discussion, it will be assumed that the steps of the method 600 are performed by the diagnosis model 110.

In a step 602 of the method 600, patient intake data is received by the diagnosis model 110. The patient intake data can be obtained from a variety of sources and reflect a variety of different types of factors, such as the example patient-specific factors described herein (e.g., symptom factors, medication factors, physical sign factors, demographics factors, social factors, diagnostic test results factors). In some examples, the patient intake data also includes risk factor data that is processed separately by the risk model 106.

The patient intake data can be provided via the input devices 214. In some examples, the patient intake data includes subjective data collected (e.g., by a MP or a virtual assistant that communicates with the patient). In some examples, the step 602 includes pre-processing of this patient intake data, using a large language model (LLM) to process the subjective patient intake data against objective information immediately available (e.g., from the databases 230). For example, to provide as much diagnosis-relevant information as possible to the machine learning models 205, a LLM of all medical publications and texts is utilized to determine what additional or repeated questions, in iterative loop fashion, should be asked about present symptoms, recent travel, history of physical and emotional traumas, environmental and zoonotic exposures, medication and supplement history, medical and surgical history, hospitalizations, family history, and the like, before assessing for diagnosis. The information obtained from the patient through this iterative process using a LLM and, e.g., a virtual assistant that receives input from the LLM indicating what additional information to request from the patient based on categories of information that are missing, becomes part of the patient intake data received at the step 602.

At a step 604 of the method 600, the diagnosis model 110 accesses information about all known human diagnoses 250 stored on the database(s) 230. In some examples, the medication information 252, 254 and 256 is also accessed by the diagnosis model 110 at the step 604.

At a step 606 of the method 600, the diagnosis model 110 determines elimination rules to eliminate some of the known human diagnoses 250 as candidate diagnoses. The elimination rules are determined based on the received patient intake data and using the diagnosis rules described above. For example, if the patient intake data indicates that the patient is male, one or more elimination rules are determined by the diagnosis model 110 that eliminate(s) all diagnoses that are specific to pregnancy complications. As another example, if the patient intake data indicates that the patient has never taken an opioid, one or more elimination rules are determined by the diagnosis model 110 that eliminate(s) all diagnoses that are specific to opioid side effects or contraindications.

The elimination rules can be determined based on the presence or the absence of a given factor for a given patient. For example, an elimination rule can be determined based on a negative test result (absence of a given factor) or based on a positive test result (presence of a given factor).

The diagnosis model 110 maps one or more pieces of patient-specific intake data to an elimination rule. The mapping can be one-to-one for some elimination rules, e.g., one patient-specific factor is mapped to one elimination rule. The mapping can be multiple to one in other examples, e.g., the combination of the patient's weight and age is mapped to one elimination rule. The mapping can be one to multiple in other examples, e.g., a patient's age is mapped to multiple discrete elimination rules.

At a step 608 of the method 600, the diagnosis model 110 applies the determined elimination rules to generate a subset of remaining candidate diagnoses from the original corpus of all possible human diagnoses. For example, at the step 608, the number of candidate diagnoses can be reduced from over 28,000 to 10 or fewer.

At a step 610 of the method 600, the diagnosis model 110 generates a diagnosis from the subset of remaining candidate diagnoses and based on the relative likelihood that each of those remaining candidate diagnoses is the actual diagnosis. In some examples, the diagnosis model 110 first generates a differential diagnosis with the subset of remaining candidate diagnoses, and then the diagnosis model 110 selects the final diagnosis from the diagnoses of the differential diagnosis.

At a step 612 of the method 600, the diagnosis model 110 outputs the final diagnosis and/or the differential diagnosis, e.g., to an output device 214.

Figure 5:
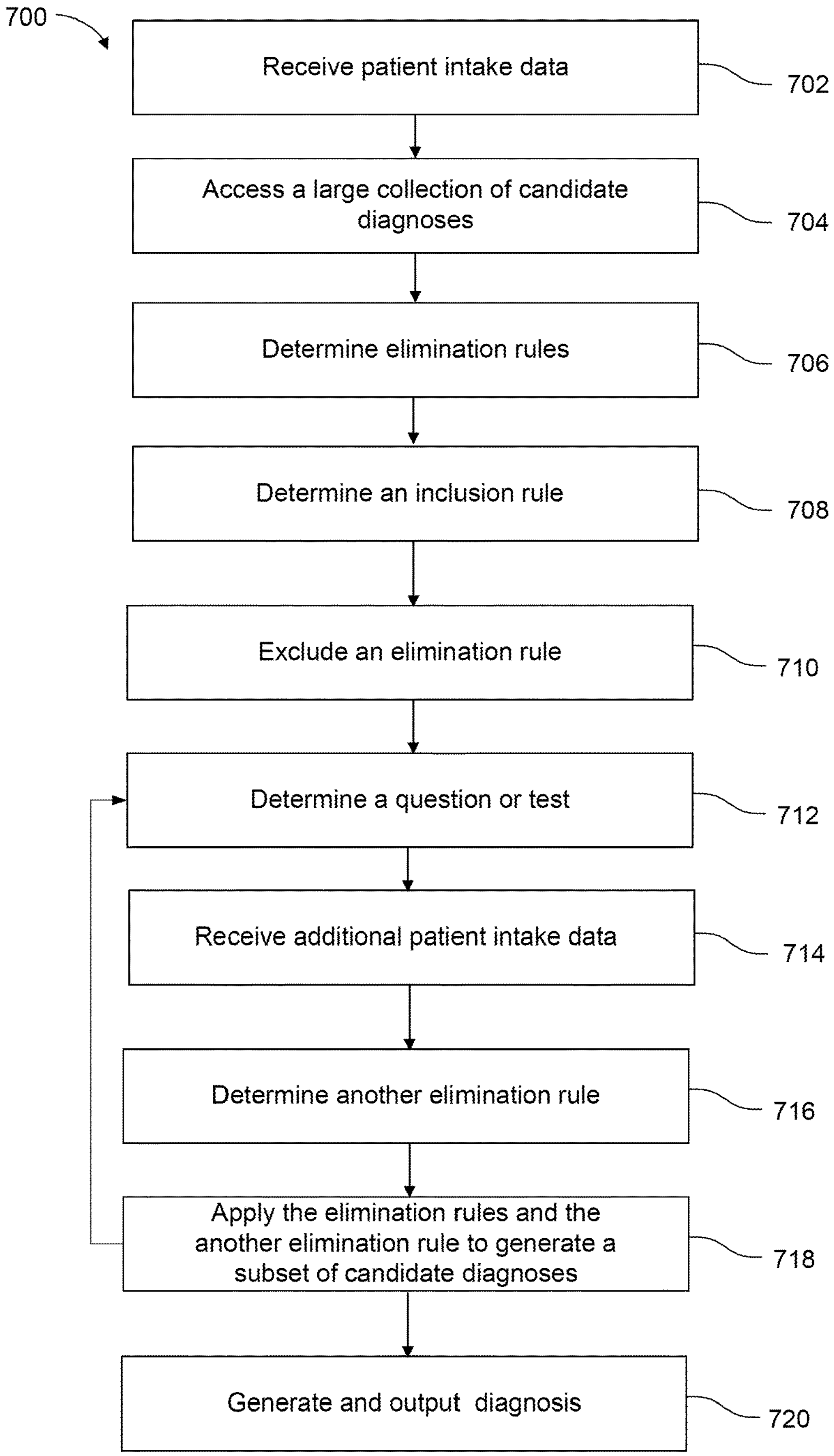
FIG. 5 depicts a further example method of generating a diagnosis in accordance with the present disclosure.

FIG. 5 depicts a further example method 700 of generating a diagnosis in accordance with the present disclosure. The method 700 embodies various methods according to the present disclosure that include subsets of the depicted steps.

In some examples, the steps of the method 700 can be performed by the computing device 202. In some examples, the steps of the method 700 can be performed by the machine learning models 205. In some examples, the steps of the method 700 can be performed by the risk model 106 and the diagnosis model 110. In some examples, the steps of the method 700 can be performed by the diagnosis model 110 only. For purposes of the following discussion, it will be assumed that the steps of the method 700 are performed by the diagnosis model 110.

In a step 702 of the method 700, patient intake data is received by the diagnosis model 110. The patient intake data can be obtained from a variety of sources and reflect a variety of different types of factors, such as the example patient-specific factors described herein (e.g., symptom factors, medication factors, physical sign factors, demographics factors, social factors, diagnostic test results factors). In some examples, the patient intake data also includes risk factor data that is processed separately by the risk model 106.

At a step 704 of the method 700, the diagnosis model 110 accesses information about all known (or at least a very large number of) human diagnoses 250 stored on the database(s) 230. In some examples, the medication information 252, 254 and 256 is also accessed by the diagnosis model 110 at the step 704.

At a step 706 of the method 700, the diagnosis model 110 determines elimination rules to eliminate some of the known human diagnoses 250 as candidate diagnoses. The elimination rules are determined based on the received patient intake data and using the diagnosis rules described above. As with the method 600, the diagnosis model 110 maps one or more pieces of patient-specific intake data to an elimination rule. The mapping can be one-to-one for some elimination rules, e.g., one patient-specific factor is mapped to one elimination rule. The mapping can be multiple to one in other examples, e.g., the combination of the patient's weight and age is mapped to one elimination rule or the combination of a patient's preexisting medical condition combined with a contraindication to that condition for a medication the patient is currently taking is mapped to a single elimination rule. The mapping can be one to multiple in other examples, e.g., a patient's age is mapped to multiple discrete elimination rules.

At a step 708 of the method 700, the diagnosis model 110 determines an inclusion rule. The inclusion rule is determined based on the patient-intake data. For example, if the patient intake data indicates that the patient has a medically unusual characteristic, such as a history of seizures, then an inclusion rule is determined whereby all candidate diagnoses that can be related to seizures are included.

The elimination rules and inclusion rules can be determined based on the presence or the absence of a given factor for a given patient. For example, an elimination rule or an inclusion rule can be determined based on a negative test result (absence of a given factor) or based on a positive test result (presence of a given factor).

At a step 710 of the method 700, the diagnosis model 110 applies the inclusion rule determined at the step 708 to exclude at least one of the elimination rules determined at the step 708. For example, if at the step 706, based on the patient intake date (e.g., a negative CT scan of the brain without contrast), the diagnosis model 110 determined an elimination rule that ruled out diagnoses specific to a brain tumor, at the step 710 that elimination rule is excluded from the elimination rules to be applied to the candidate diagnoses.

At a step 712 of the method 700, a question (e.g., have you been experiencing any chest pain?), a test (e.g., a blood test, a urine test, a saliva test) or other diagnostic tool (e.g., imaging) is determined by the diagnosis model 110 to elicit additional patient-specific intake data. For example, following the steps 706, 708 and 710, the diagnosis model 110 can determine that it does not have sufficient information to generate a sufficiently specific differential diagnosis or to generate a needed final diagnosis.

For example, the diagnosis model 110 can be configured to evaluate the suitability of potential differential diagnoses and final diagnoses based on one or more predefined threshold confidence scores associated with the potential differential diagnoses. For example, if a potential differential diagnosis lacks any possible diagnosis with a likelihood of at least 10 percent, then the diagnosis model 110 can automatically disqualify that potential differential diagnosis and perform the step 712 of the method 700 to elicit more patient-specific information to improve the reliability of the differential diagnosis. As another example, if a potential differential diagnosis includes too many diagnoses (e.g., more than a predefined number, such as more than one or more than two) that are within a predefined likelihood (e.g., 2 percent) of one another, then the diagnosis model 110 can automatically disqualify that potential differential diagnosis or final diagnosis and perform the step 712 of the method 700 to elicit more patient-specific information to improve the reliability of the differential diagnosis. The diagnosis model 110 can apply other such rules to determine if a given possible differential diagnosis or final diagnosis is sufficiently specific and has sufficient confidence of accuracy (and therefore is sufficiently meaningful) or if more information is needed.

The additional information determined to be elicited at the step 712 can be targeted by the diagnosis model 110 to try to eliminate, confirm, decrease or increase the likelihood of specific candidate diagnoses. For instance, at the step 712 a follow-up CT scan of the brain with contrast is recommended for the patient to eliminate or increase the likelihood of diagnoses specific to brain tumors. As another example, the intake data indicates that the patient has a preexisting medical condition and is currently taking a given medication, and it is determined from the medication contraindications 256 that there is a contraindication to that preexisting condition for the medication the patient is currently taking, then the additional information to be elicited can be targeted to determine if the patient is suffering from a symptom known to be a result of that contraindication. As another example, if the intake data indicates the patient has hypertension and has another symptom or physical sign that could be indicative of a side effect of certain anti-hypertensive medications, then the additional information to be elicited can be targeted to determine if the patient is taking or has taken any anti-hypertensive medications.

If a question is generated at the step 712, the question can be presented to the patient by a MP or by a virtual assistant configured to receive, via an input device, the patient's response to the question.

At a step 714 of the method 700, the additional patient intake data in response to the question, test or other diagnostic determined at the step 712 is received, e.g., via the input device(s) 216. For example, a CT scan with contrast, or a speech-to-text transcribed uttered answer to a question from a patient to a virtual assistant is provided to the diagnosis model 110 via the input device(s) 216.

At a step 716 of the method 700, the diagnosis model 110 determines at least one other elimination rule based on the additional data received at the step 714 and using the diagnosis rules that the diagnosis model previously learned as described above. For example, the CT scan with contrast can indicate the presence of a brain tumor, and as a result a further elimination rule is determined to rule out from the remaining candidate diagnoses any diagnoses that are inconsistent with the existence of a brain tumor.

At a step 718 of the method 700, the additional elimination rule(s) determined at the step 716 are applied by the diagnosis model to the remaining candidate diagnoses to generate a subset (or second, smaller subset) of candidate diagnoses.

The steps 712, 714, 716 and 718 can be repeated by the diagnosis model 110 in a feedback loop as many times as needed to arrive at a differential diagnosis or single, final diagnosis that satisfies the predetermined confidence thresholds or other predefined specificity requirements for a differential diagnosis and/or final diagnosis output by the diagnosis model 110.

At a step 720, once a suitable differential diagnosis or final diagnosis is possible, that differential diagnosis and/or final diagnosis is generated by the diagnosis model 110 and output via the output device(s) 214.

Figure 6:
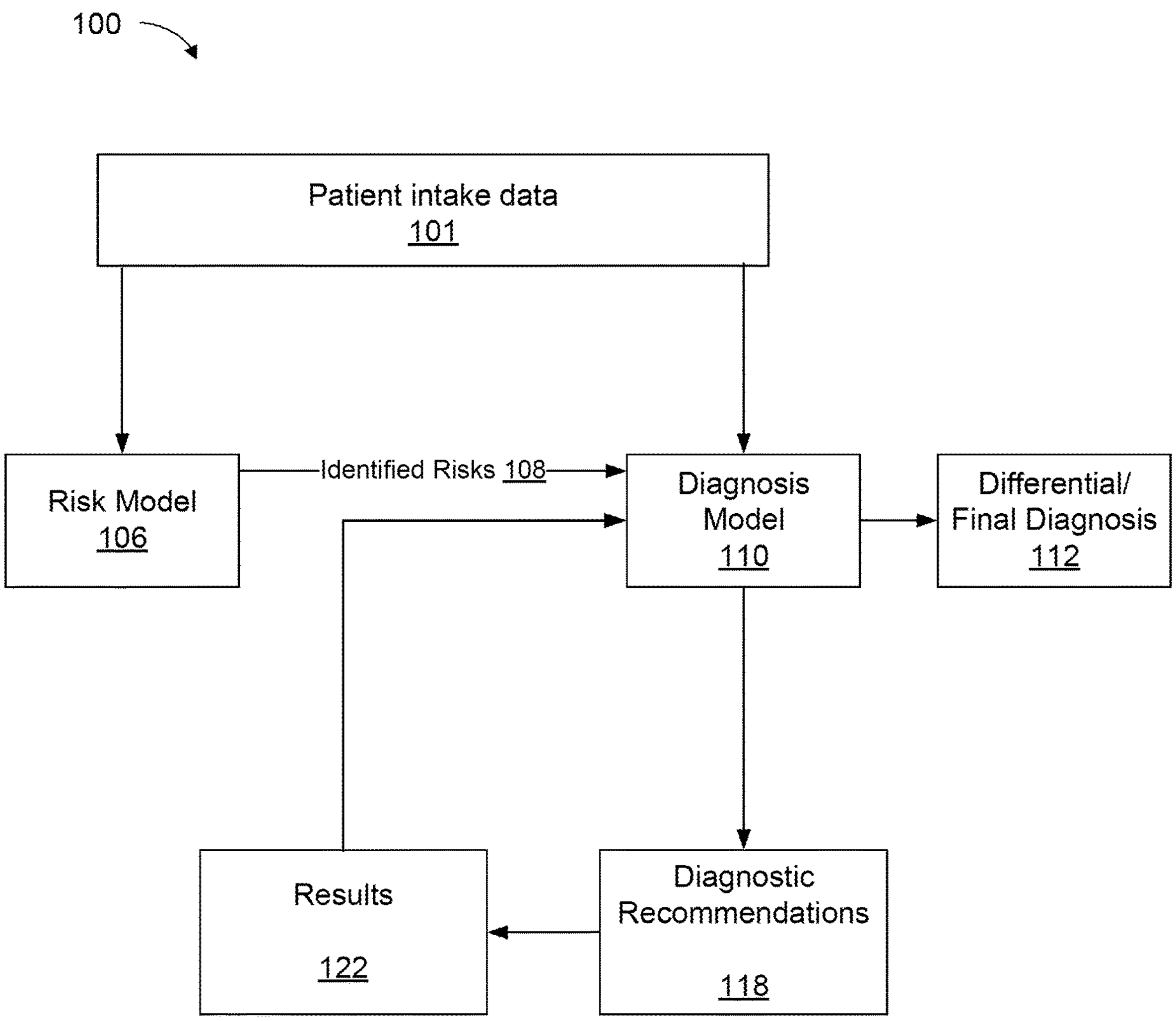
FIG. 6 depicts a further example method of generating a diagnosis using components of the system of FIG. 1 in accordance with the present disclosure.

FIG. 6 shows a further example method 100 of generating a differential diagnosis and/or final diagnosis in accordance with the present disclosure, and using components of the system 200 of FIG. 1. The method 100 embodies various methods according to the present disclosure that include subsets of the depicted steps.

At a step 102 of the method 100, a comprehensive medical history is obtained from a patient to generate patient intake data 101. The patient intake data 101 can include any or all of the types of intake data described herein. The patient intake data 101 can correspond to the patient intake data described in connection with the methods 600 and 700.

Obtaining the patient intake data 101 from the patient can be performed by engaging the patient with a virtual assistant presented to the patient via the output device(s) 214 and receiving information from the patient via the input device (s) 216. For example, the virtual assistant or agent can ask the patient questions textually via a display device or with synthesized speech via a speaker and the patient can answer the questions orally (with natural utterances) into a microphone or by selecting options or entering text via a touch screen or other input device. For example, speech-to-text (STT) and text-to-speech (TTS) algorithms run by the computing device 202 can support the user's interaction with the virtual assistant via both voice and text. Natural Language Understanding (NLU) and Generative Large Language Models (GLLM) can process the user's inputs during the interview with the virtual assistant in order to detect intents and extract the relevant intakes in a structured form so that it can be run sequentially through two consecutive machine learning models described below. Features of the virtual assistant, and how input data from the patient is obtained, interpreted and processed using the virtual assistant is described in U.S. Pat. No. 11,404,170.

In some examples, at least some of the intake data (risk data in particular) is pre-stored in a database from one or more previous interviews with the patient that elicited information from the patient related to risk factors. This data is then accessed by the machine learning models herein and combined with the current symptom and physical sign data and/or additional risk data obtained from a current interview of the patient to generate a differential diagnosis.

Physical sign data is data that may relate to or complement a disease symptom or medical complaint of the patient, and/or that may indicate a pathology or otherwise have pathological significance. Non-limiting examples of physical signs include absent bowel sounds, an enlarged lymph node, palpable liver, crackles on a lung exam, a heart murmur on a heart exam, leg edema, and the like.

The virtual assistant can obtain any intake data about the patient that may be relevant to making a differential diagnosis for the patient. Such data can include, for example, health risk data related to one or more hereditary factors, familial factors with no known genetic mutations, environmental exposure factors, lifestyle factors, social determinants of health factors, demographic factors, mental health factors, and preventive measure utilization risk factors, and also analyze patient-reported symptoms, patient-denied symptoms, related history of present illness, physical signs, past medical history, current and past medications, age, gender, and ethnicity. Such intake data can also include data related to one or more symptoms the patient is experiencing, such data that identifies one or more symptoms, and any additional related information to the symptoms such as previous history of similar symptoms, recent exposures that may have contributed to the symptoms, when, where, and how the symptom started, any known triggers, what parts of the body are affected, what relieves and/or worsens the symptom, if anything, how the symptom has changed since it first appeared, etc. The intake data can also include data reflecting other relevant information for the patient for purposes of making a differential diagnosis such as past and present medical history, past surgeries, medications, allergies, recent travel, trauma, exposures, past test results, published case studies, etc.

The intake data can also correspond to the absence of one or more symptoms, physical signs, family history, exposures, and the like, as such absence of data may relate to one or more diseases. For example, the absence of a positive monospot test, swollen nodes, and an enlarged spleen can rule out mononucleosis as the cause of a sore throat. As another example of intake data corresponding to the absence of a physical sign, the absence of an elevated blood sugar can rule out diabetes. As another example of intake data corresponding to the absence of a physical sign, the absence of a noisy lung can rule out pneumonia. As an example of intake data corresponding to the absence of a risk factor, a negative genetic test for Huntington Chorea can rule out that disease.

The intake data can be obtained by asking the patient, e.g., via a virtual assistant, many questions about the presence and/or absence of associated symptoms, risk factors, social factors, demographic factors, medication factors, and physical signs to help rule out disease. For example, for a patient complaining of headache and nausea, the patient can be asked if there are associated symptoms such as a fever, chills, dizziness, loss of vision, blurred vision, facial drooping, facial paralysis, vomiting, shortness of breath, chest pain, abdominal pain, back pain, diarrhea, constipation, and the like. The absence of these symptoms sometimes associated with headaches caused by other conditions, more strongly suggests a migraine headache over something more systemic like a flu (fever, chills), food poisoning (nausea, vomiting, diarrhea, abdominal pain), or stroke (loss of vision, blurry vision, nausea, dizziness, facial paralysis, facial drooping).

That is, the absence of some symptoms, physical signs, and/or risk factors can point to some diagnoses while the presence of the same or other symptoms, physical signs, and/or risk factors can point to other diagnoses. In this manner, collected patient intake data that corresponds to the absence of one or more symptoms, physical signs, or risk factors, can be used by the diagnosis model to generate a more accurate differential diagnosis, e.g., by generating elimination rules or inclusion rules as described above.

As mentioned, the intake data can include physical sign data. In addition to the virtual assistant, physical sign data can be obtained directly from the patient or from another source, such as a physician or other MP who has reviewed or used AI to review imaging or other testing of a patient (e.g., an electrocardiogram or chest x-ray of the patient). Physical sign data can be obtained directly from a sensor, an automaton, physician or other MP who has performed a physical examination of the patient, such as an external lymph node examination or an external examination of the liver. Physical sign data can be obtained from a database storing previously recorded and stored electronic medical records of the patient that include physical sign data. Physical sign data can also be obtained in an automated fashion from the patient at or about the same time as the patient's interview with the virtual assistant. In this context, the physical sign data can be obtained by one more of the input devices 216 of the computing device 202, for example, by receiving data collected from a device such as a medical instrument examining the patient, such as a camera that detects edema or an enlarged palpable lymph node.

Non-limiting examples of devices that can collect intake data will now be described.

The intake data can be collected using a microphone that captures oral responses generated by the patient in response to questions by a virtual assistant and/or a microphone that captures physiological sounds generated by the patient's body (e.g., a heart murmur).

The intake data can be collected using a visual camera that captures images of the patient (e.g., images of the skin, eyes, inside the ears, inside the mouth).

The intake data can be collected using a thermometer that measures a body temperature of the patient.

The intake data can be collected using a blood pressure meter that measures a blood pressure of the patient.

The intake data can be collected using an oximeter that measures an oxygen concentration in blood of the patient.

The intake data can be collected using a pulse meter that measures a heart rate of the patient.

The intake data can be collected using a glucometer that measures the blood glucose level of the patient.

The intake data can be collected using a portable ultrasound device that can identify masses or structural abnormalities.

The intake data can be collected using an electrocardiogram (ECG) machine that measures the patient's heart rate, waveform pattern, and electrical activity.

The intake data can be collected using an electroencephalogram (EEG) machine.

The intake data can be collected using a magnetic resonance imaging (MRI) machine that identifies detailed images of nearly every normal and abnormal structure and organ inside the body of the patient.

The intake data can be collected using radiography (x-ray) that identifies images of certain structures and organs inside the body of the patient.

The intake data can be collected using a cat scan (CT) that identifies slices, or cross-sections, of the body inside the body of the patient.

The intake data can be collected using a positron emission tomography (PET) scan that shows how organs and tissues are working inside the body of the patient.

The intake data can be collected by a sensor capable of detecting normal and abnormal anatomy, physiology, and or histology.

The intake data can be collected by a robot or automated humanoid able to detect normal or abnormal anatomy, physiology, and or histology.

Other medical devices and instruments can be used to obtain the intake data.

As mentioned above, the intake data, or portions thereof, can also be pre-stored in a database and collected from the database.

According to the method 100, once collected, the intake data is parsed (e.g., by one or more machine learning models or software modules) into at least two groups. The at least two groups can include a symptom data subset of the intake data that relates to the presence or affirmative absence of one or more physical symptoms of the patient and a risk data subset of the intake data that relates to a predisposition of the patient to each of a plurality of diseases independently of the one or more symptoms being experienced and based on the presence or affirmative absence of one or more risk factors. For instance, the symptom data could include a sore throat, and physical sign data could include swollen neck lymph nodes and tonsillar exudate, while the risk data could include a grandparent who died of leukemia and/or recent exposure to someone diagnosed with *streptococcus* (strep) throat or infectious mononucleosis. The intake data can be parsed into other groups of data as well, such as social data, demographic data, medication data, and the like.

In some examples, a machine learning model is trained, based on a corpus of data with known categorizations, to accurately parse the data into a risk data category on the one hand, and a symptom data (and, in some examples, other data such as physical sign data, medication data, social data, demographic data) category on the other hand, based on one or more parameters of the intake data, e.g., based on the content of a question asked of the patient that elicited the data. For instance, if the data is derived from a response by the patient to the question of "how are you feeling today", then the data is categorized as symptom data. If the data is derived from a response by the patient to the question of "have any of your parents or grandparents been diagnosed with heart disease", then the data is categorized as risk data. As another example, if the data is derived from a measurement by a thermometer, a blood pressure meter, a pulse meter, an oximeter, an x-ray, CT scan, PET scan, MRI, or from a visual image of a lesion on the patient's skin, then the data is categorized as symptom data, whereas if the data is derived from results of a genetic test, the data is categorized as risk data. As another example, if the data is physical sign data, then the data is categorized as symptom data, whereas if the data relates to the patient's race, then the data is categorized as risk data.

Other data parameters can be used to parse the data into risk data and symptom data.

As part of the method 100, risk data is provided to the risk model 106, which can correspond to a machine learning model of the computing device 202. The risk model 106 can, e.g., based on the parsed out risk data input into the model, predict/identify known risks for major health conditions for the patient, including but not limited to heart diseases, cancers, type 2 diabetes, stroke, and obesity, etc., and generate a reason for the increased risk. For example, the risk model can determine a risk percentage (e.g., a likelihood of the patient having the major health condition) for each of a predetermined or learned set of major health conditions based on the risk data input. As part of the method 100, the risk model 106 can generate a list of the identified risks 108. The list can be curated by the risk model 106. For example, the list can include only those health conditions having at least a predefined likelihood (e.g., 5 percent) or can include only the top N most likely health conditions, where N is a positive integer greater than zero. In some examples, the list includes every candidate diagnosis that has a non-zero percent likelihood.

As part of the method 100, the identified risks and the symptom data are provided to the diagnosis model 110 to generate a differential diagnosis and, in some examples, a list of recommended tests, questions for the patient or other diagnostics to narrow the list of possible diagnoses. The diagnosis model 110 generates a diagnosis 112 (e.g., a final diagnosis and/or a differential diagnosis) based on the symptom data (and/or all non-risk data) and the identified risks data. The candidate diagnoses generated by the diagnosis model in the differential diagnosis can be curated by the diagnosis model. For example, the differential diagnosis can include only those health conditions having at least a predefined likelihood (e.g., 5 percent) or can include only the top N most likely health conditions, where N is a positive integer greater than zero. The candidate diagnoses of the differential diagnoses can be generated in any suitable order, such as ranked by descending likelihood. The candidate diagnoses can be paired with explanations for their likelihood (and presented to the user), such as descriptions of one or more risk factors identified from the risk data. Differential diagnoses can be generated consistent with these characteristics according to the methods 600 and 700 as well.

In some examples, the differential diagnosis or final diagnosis generated can be based on matching the collected intake data 101 against published medical association guidelines. For example, the computing device 202 can access, using the communication connection(s) 218, a database(s) 230 As described above, the database(s) 230 can store known medical data about diseases from which the machine learning model(s) can derive and learn how certain symptoms and absence of certain symptoms, certain physical signs and absence of certain physical signs of, certain risk factors and absence of certain risk factors, and other intake data may correlate to specific diseases. For instance, the database(s) 230 can include tables or other data constructs of diseases that link the diseases to their related list(s) of symptoms, absence of symptoms, risk factors, absence of risk factors, physical signs, absence of physical signs, social factors, absence of social factors, demographic factors, absence of demographic factors, medication factors, absence of medication factors, and the like.

The machine learning model(s) matches the patient intake data against the known medical data, e.g., using the diagnosis rules described above, to generate the differential diagnosis and/or final diagnosis. For instance, many diseases have overlapping symptoms such as fever, pain, nausea, headache, sore throat, etc. and/or overlapping risk factors, such as obesity, a genetic disorder, environmental exposures, etc. A trained diagnosis model 110 determines a probability of each of a plurality of candidate diagnoses by comparing the suite of intake data against the database's 230 data of known diagnoses, medication data and other information, and their correlations, and determining matches to different diagnoses at various levels of confidence. The confidence levels correspond to the probabilities of the candidate diseases in the generated differential diagnosis.

In many scenarios, the patient intake data includes many parameters (e.g., dozens or even hundreds or thousands) due to the many questions asked of the patient about their symptoms and family history, as well as all the other data that is included, such as physical sign data, social data, medications data, demographics data, etc. The machine learning model(s) include one or more algorithms for generating a differential diagnosis and learn over time to more accurately weight the many parameters in the differential algorithm(s) to generate more and more precise differential diagnoses.

In some examples, patient risk data is matched to known medical data derived from the database 230 separately from the patient symptom (and other non-risk) data being matched to known medical data. In some examples, medication data is also matched separately to known medical data from risk data, symptom data, and other non-risk and non-medication data.

For example, the risk model 106 can perform a matching operation with disease-risk factor (and/or absent risk factor) pairings stored in the database(s) 230, and feed the results of that matching to the diagnosis model 110. The diagnosis model 110 then uses the risk factor matching results and matching results of the patient symptom (and/or absent patient symptom) and related data to generate the differential diagnosis. The matching results of the patient symptom and related data can be determined by the diagnosis model 110, or another model different from the risk model. Other subsets of the intake data 101, such as medication data) can be parsed out and processed separately (like the risk data) and the resulting identified correlations (such as identified medication side effects or contraindications) can be fed to the diagnosis model 110.

In some examples of the method 100, a list of candidate diagnoses in the differential diagnoses are paired by the diagnosis model with or correlated to specific risks identified for the patient.

The diagnosis 112 can also include one or more treatment recommendations or other recommended interventions, such as prescribing a medication or deprescribing a medication. For instance, if the diagnosis indicates that the patient's condition is a result of medication side effect, the diagnosis 112 generated by the diagnosis model 110 can recommend, via the output devices 214, to discontinue (and deprescribe) a medication the patient is currently taking and/or prescribe a different medication in its place.

As part of the method 100, the diagnosis model 110 can determine one or more tests, additional patient questions or other diagnostics (e.g., blood tests) 118 to confirm or rule out one or more of the candidate diagnoses, similar to the step 714 of the method 700.

The method 100 can include a consideration and approval phase of the recommended diagnostics. Once approved, the diagnostics are performed.

The results 122 of the diagnostics 118 (e.g., results of recommended blood tests) are provided to the diagnosis model 110 as part of the method 100. The diagnosis model 110 then refines the previous differential diagnosis list based on the diagnostics results to generate an updated differential diagnosis and/or final diagnosis and correlated risk factors modified based on the additional diagnostics data. For example, if a blood test result rules out one or more of the candidate diagnoses of the original differential diagnosis or the original final diagnosis, the updated differential diagnosis or final diagnosis may include only a narrowed down subset of the candidate diagnoses of the original differential diagnosis or final diagnosis, and/or with modified percentages for each candidate diagnosis in the case of a differential diagnosis output.

In some examples, the updated differential diagnosis or final diagnosis may include a candidate diagnosis that was not included in the original differential diagnosis or original final diagnosis, e.g., if the additional diagnostics revealed the possible presence of a heath condition not previously considered.

In some examples, the steps of the loop illustrated by the blocks 110, 118 and 122 can then be repeated based on the updated differential diagnosis or final diagnosis in a feedback loop that can be repeated until no more diagnostics are indicated and/or there is sufficient confidence in a single, final diagnosis.

Once the differential diagnosis is refined and finalized, the method 100 can include that all the patient findings and recommendations are presented, e.g., via one or more graphical user interfaces, speakers, and/or other output devices 214. Output data can be presented via one or more dashboards on a graphical display that summarize the main clinical findings and recommendations such as risk assessment, differential diagnosis and/or final diagnosis and their correlation with the identified risks as well as lab test recommendations and references to medical studies supporting the provided recommendation, medications to prescribe or deprescribe, other interventions to perform, and the like. Generative Large Language Models can be applied to both patient data and provided recommendations to automate their documentation in a structured way that aims to make it possible to integrate them with the main electronic medical records and improve future analysis of the patient's conditions, encounters and history.

The methods 100, 600 and 700 can provide at least one or more of the following advantages: ensuring that risk factors, medication factors, social factors, demographic factors, symptom factors, physical sign factors and other factors are fully considered as part of the differential diagnosis or final diagnosis; generating list of all reasonably possible diagnoses tied to both risks, symptoms and other factors; advising physicians and other clinicians as to what further testing is indicated and could be completed pre-visit to aid diagnosis at the point of care; initiating warranted testing/diagnostics; feeding test/diagnostics results back into the diagnosis model to generate a new list of diagnoses and/or a final diagnosis as part of a feedback loop; generating further testing, if needed, to further narrow down diagnoses; and rendering differential diagnoses and/or final diagnoses that are both less underinclusive and less over inclusive by starting with a corpus of all known diagnoses and then determining elimination rules to drill down to a reliable and specific differential diagnosis or final diagnosis.

It will also be appreciated that the machine learning models (such as the diagnosis model 110 and the risk model 106) will learn additional correlations, parameters, and parameter weights as among symptom data and risk data in generating candidate diagnoses as the models are used on more and more data (e.g., with more and more patients), such that the models' accuracy and ability to accurately generate reliable differential diagnoses and final diagnoses will continuously improve.

In addition, the machine learning models will learn how to optimize testing/diagnostics recommendations for different differential diagnoses and/or final diagnoses according to optimization schemes as described herein. For instance, the machine learning models will learn which tests, other diagnostics and patient data are more efficient at ruling out candidate diagnoses in a given differential diagnosis, or what is most likely to be the most efficient order in which to administer tests/diagnostics to rule out candidate diagnoses as quickly as possible, and thereby minimize the number of feedback loops of testing and differential diagnosis generation needed to arrive at a definitive diagnosis, shortening the time to a definitive diagnosis, and reducing the cost (e.g., via less testing) of obtaining a correct diagnosis. That is, the machine learning model(s) can receive, as input, the model (s)' own previous outputs to continuously train the model(s) to generate more accurate differential diagnoses and/or final diagnoses and more efficient testing/diagnostics recommendations. For instance, for a given differential diagnosis or final diagnosis, a model may learn over time, based on results of prior testing recommendations for the same differential diagnosis or final diagnosis, to recommend a blood test before a CT-scan of the head to more quickly and/or cost-effectively reach a definitive diagnosis.

Figure 7:
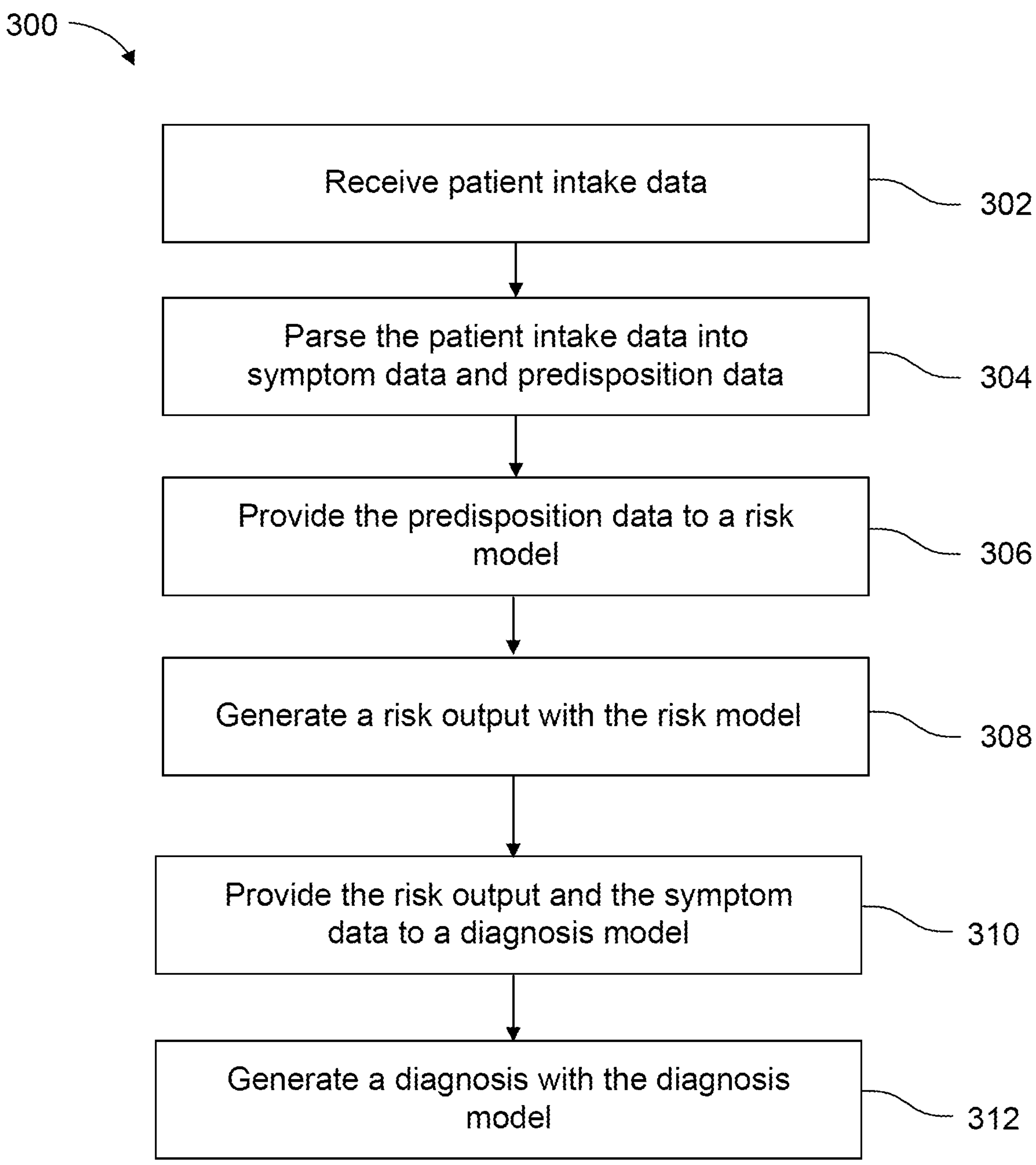
FIG. 7 depicts a further example method of generating a diagnosis in accordance with the present disclosure.

FIG. 7 shows a further example of method 300 generating a differential diagnosis in accordance with the present disclosure. The method 300 can be performed by components of the computing device 202 (FIG. 1), including the machine learning models 205.

At a step 302 of the method 300, patient intake data (e.g., intake data 101) for a given patient is received (e.g., collected), as described above.

At a step 304 of the method 300, the intake data is parsed into symptom data (including data corresponding to absence of symptoms) and predisposition data (including data corresponding to absence of predispositions). Parsing is performed based on parameters of the intake data, as described above. Predisposition data refers to data, such as risk data, that indicates a predisposition of the patient to each of a plurality of diseases (e.g., predefined, major health conditions) independently of the one or more physical symptoms or physical signs data (e.g., independently of the symptom data that is parsed).

At a step 306 of the method 300, the predisposition data is provided to a risk model.

At a step 308 of the method 300, the risk model generates a risk output based on the predisposition data. For example, the risk model generates a list of identified risks and likelihoods, as described above.

At a step 310 of the method 300, the risk output and the symptom data are provided to a diagnosis model.

At a step 312 of the method 300, the diagnosis model generates a differential diagnosis based on the risk output and the symptom, and as described above.

The steps 306 and 308 are performed independently of, and prior to, the steps 310 and 312.

In some examples, other categories of non-symptom data, such as medication data, can be handled separately from the symptom data similar to the steps 306 and 308 and then the corresponding outputs are fed to the diagnosis model. For example, medication data can be parsed and then processed separately to generate a medication output, such as list of identified relevant medication side effects and/or contraindications for the patient based on the medication data parsed from the intake data 101 (e.g., medications taken by the patient and not taken by the patient, dosage, when the patient took the medication, as well as non-patient specific medication data such as known side effects and contraindications of the medications the patient was taking derived from database(s) 230). Such medication output is then provided to the diagnosis model, similar to the step 310 with respect to the risk data, and the differential diagnosis is based in part on mapping the medication output together with the symptom and other intake data to possible diagnoses based on the algorithms developed by the machine learning models 205 and using the databases identifying all known human medical diagnoses.

In some examples, the steps 306 and 308 relating to risk data collection and processing and/or analysis can be performed at a time before the patient is even experiencing the current symptoms or physical signs from which the symptom data is derived. For example, collection of risk data that is independent of any symptom data and performance of risk analysis of the risk data independently of any symptom data analysis, can be performed over months or years based on interactions and/or tests from different visits by the patient with health care providers, including, e.g., regular check-ups without any symptoms or physical signs, and such risk data can be stored in a database. Then, when the current symptoms are present, the risk factor analysis that has already been performed is automatically retrieved from the database and processed by the diagnosis model.

Thus, at the diagnosis generation stage of the method 300, the patient's risk factors and predispositions and the patient's non-predispositions (e.g., the diseases and/or other conditions ruled out as risks by the steps 306 and 308) and, in some examples, the patient's medication history have already been determined and inform or modify how the diagnosis model processes and analyzes the symptom data and other data (e.g., physical sign data), such that an initial differential diagnosis or initial final diagnosis can be generated more quickly and accurately.

As the number of weighted parameters of an algorithm increases linearly, the magnitude of computer processing power needed to process the algorithm to generate an output increases exponentially. Because the risk data has already been processed, the number of parameters needed to be modeled and matched by the diagnosis model algorithm(s) can be significantly reduced, resulting in a quicker diagnosis that consumes fewer computing resources.

Similar computational efficiencies can be gained by employing the eliminations rules features of the present disclosure describe above, such as those embodied in the methods 600 and 700.

Because the risk data and symptom data are parsed, separated from each other, and processed separately, the generated differential diagnosis and/or final diagnosis can also be more accurate, because there is a smaller chance, or no chance that, e.g., symptom data is somehow conflated by the diagnosis model algorithm(s) with, or interpreted as, risk data or medication data. For example, in the case of a patient who presents with high blood pressure, if there is no determination or categorization of the high blood pressure data as between risk data and symptom data, it is possible that the high blood pressure data could be assigned too much weight as indicating a predisposition for heart disease (thereby generating an inaccurately skewed differential diagnosis) despite there being an absence of actual predisposition or risk data for heart disease (e.g., there is no family history of heart disease or genetic propensity for heart disease) or the taking of a medication that could cause temporary hypertension.

Figure 8:
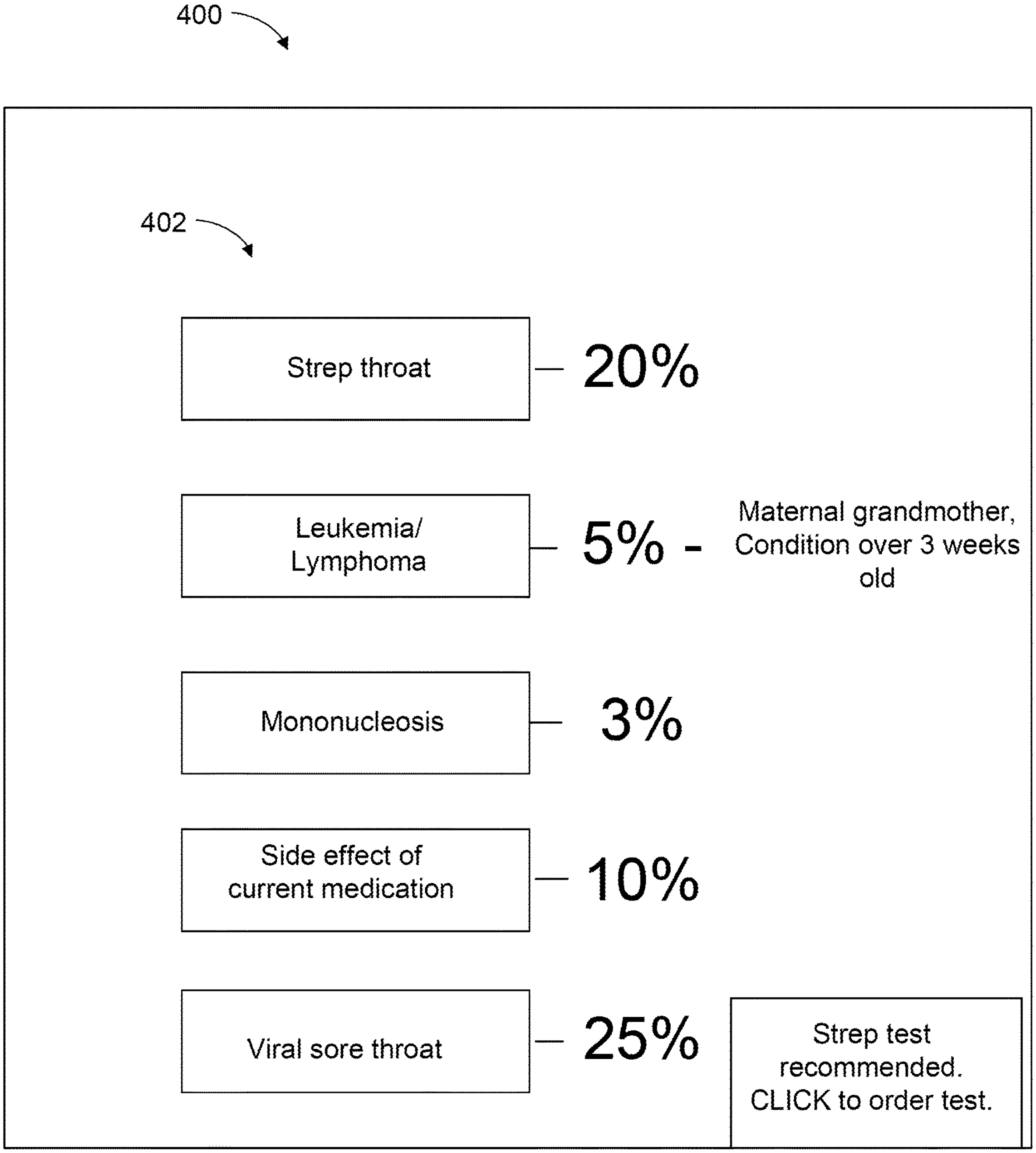
FIG. 8 depicts an example user interface generated by the system of FIG. 1.

FIG. 8 shows an example user interface 400 generated by an output device 214 of the system 200 of FIG. 1. The content of the information displayed on the user interface 400 is generated by the machine learning models 205 of the computing device 202 of FIG. 1.

The user interface 400 includes a differential diagnosis 402. In this example, the differential diagnosis includes both major health conditions and at least one non-major health condition (viral sore throat). In other examples, only predefined major health conditions are listed. In other examples, only health conditions that require further testing to confirm or rule out are listed.

The differential diagnosis 402 lists all candidate diagnoses (strep throat, leukemia/lymphoma, mononucleosis, side effect of current medication, viral sore throat) that meet some predefined threshold likelihood (e.g., above 0 percent, or above 1 percent). The list can be provided in any suitable order. In the example shown, the major medical conditions are listed first, and according to descending probability.

The interface 400 can provide an explanation or basis for one or more of the candidate diagnoses, particularly those with serious long term implications or that may require expensive testing to confirm or rule out. In this example, just the leukemia/lymphoma candidate diagnosis includes associated therewith a basis (the maternal grandmother was diagnosed with leukemia/lymphoma (risk data) and the sore throat has persisted for more than three weeks (symptom data)).

Figure 9:
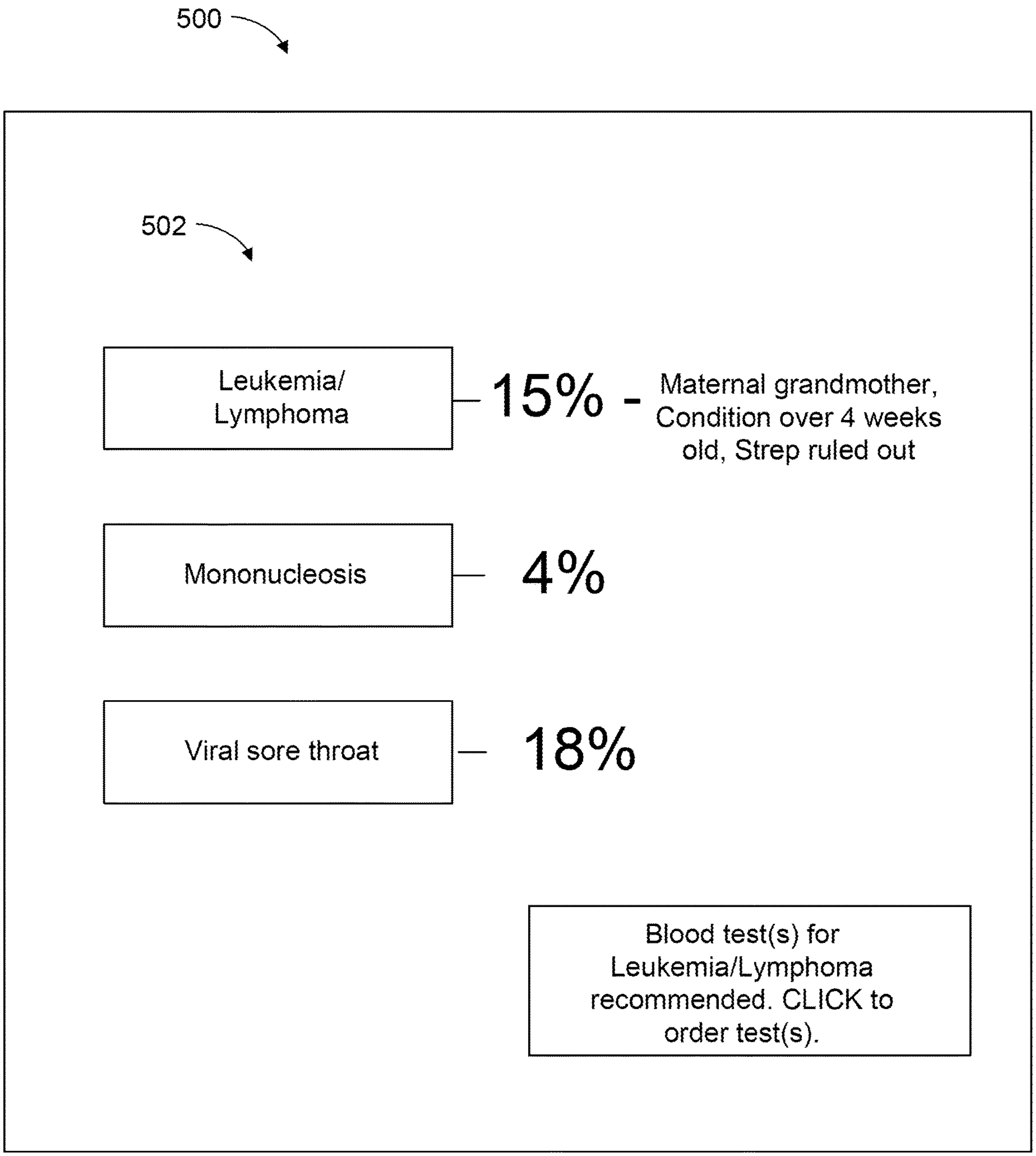
FIG. 9 depicts a further example user interface generated by the system of FIG. 1.

The interface 400 also includes a recommendation for further testing. In this case, a strep test is recommended based on the likelihood that the condition is strep throat. If strep is ruled out by the strep test, that negative test result can be provided to the diagnosis model, which can then generate an updated user interface 500 (FIG. 9) with an updated differential diagnosis 502 that includes just leukemia/lymphoma, mononucleosis, and viral sore throat (in some examples, with adjusted likelihoods e.g., based on the fact that sore throat has now persisted for even longer and the fact that strep was ruled out). The updated user interface 500 may at that point recommend one or more blood tests to confirm or rule out leukemia/lymphoma. This process can be repeated until a single diagnosis is reached with sufficient confidence. Over time, the process can be updated to e.g., recommend a different type or a different order of tests in order to narrow down the initial differential diagnosis more quickly.

In alternative examples, the user interface can recommend multiple tests or other diagnostics at the same time to confirm or rule out multiple candidate diagnoses. For instance, the same user interface can include recommendations for a strep test, blood work for leukemia/lymphoma and a monospot test for mononucleosis. Each recommended test can, in some examples, be selectable (e.g., by clicking on a graphical element) so that the recommended test can be easily ordered.

Although specific embodiments are described herein, the scope of the technology is not limited to those specific embodiments. Moreover, while different examples and embodiments may be described separately, such embodiments and examples may be combined with one another in implementing the technology described herein. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A computer-implemented method for generating a diagnosis of a human disease of a patient, comprising:

receiving unstructured data, including medical journals;

cleaning the unstructured data to generate cleaned data;

converting the cleaned data into a standardized format, the standardized format including a table having rows and columns;

training at least one machine learning model using the table to generate at least one trained machine learning model;

receiving, with the at least one trained machine learning model and via an input device, patient intake data related to the patient;

accessing, with the at least one trained machine learning model and from at least one database, a collection of at least 7,000 candidate human medical diagnoses;

determining, by the at least one trained machine learning model, a plurality of elimination rules for a candidate diagnosis elimination process, wherein the plurality of elimination rules are based on the patient intake data, wherein the at least one trained machine learning model includes a Process Reward Model (PRM) combined with a Tree of Thoughts (TOT) method of reasoning including a tree, the PRM being configured to assess and score each step of the candidate diagnosis elimination process, and the TOT method being configured to navigate through a plurality of reasoning steps by adjusting a route through branches of the tree based on both prior conclusions and future assertions to identify a possible path to the diagnosis, the possible path including requesting and receiving additional patient intake data to rule out at least one candidate diagnosis;

applying, by the at least one trained machine learning model, the plurality of elimination rules to the collection to generate a subset of candidate human medical diagnoses from among the collection;

generating the diagnosis based on the subset, the diagnosis including one of the medical diagnoses from among the subset; and outputting, using the at least one trained machine learning model, to a user interface of an output device:

the diagnosis; and an explanation for the diagnosis, the explanation including both symptom data and non- symptom risk data obtained from the patient intake data.

2. The computer-implemented method of claim 1, wherein the collection includes at least 28,000 candidate human medical diagnoses.

3. The computer-implemented method of claim 1, wherein the plurality of elimination rules are determined based on factors of the patient derived from the patient intake data, the factors including one or more of: age, gender, race, a blood test result, a urine test result, a genetic test result, an absent radiographic finding, a present radiographic finding, an ultrasound result, a biopsy result, an absent physical sign finding, a present physical sign finding, an absent symptom, a present symptom, an absent personal medical history, a present personal medical history, an absent history of exposures, a present history of exposures, an absent history of traumas, a present history of traumas, a present history of pregnancy, a family history, an electrocardiogram result, an electroencephalogram result, a negative peripheral smear, positive peripheral smear, a negative culture, a positive culture, a drug history, a drug allergy, a drug side effect, a drug contraindication, an interaction between drugs, an interaction between a drug and food, an absent patient risk factor, a present patient risk factor, socio-ethnic- economic classification, and geographic location.

4. The computer-implemented method of claim 1, further comprising:

determining, by the at least one trained machine learning model, at least one inclusion rule based on the patient intake data; and excluding, by the at least trained one machine learning model, one of the plurality of elimination rules based on the at least one inclusion rule such that the one of the plurality of elimination rules is not applied by the at least one trained machine learning model to the collection.

5. The computer-implemented method of claim 1, further comprising:

determining, by the at least one trained machine learning model, an insufficiency in the plurality of elimination rules;

generating, with the at least one trained machine learning model and based on the patient intake data, at least one question to pose to the patient or at least one test to administer to the patient;

receiving, with the at least one trained machine learning model, the additional patient intake data based on at least one answer to the at least one question or at least one result of the at least one test; and determining, by the at least one trained machine learning model, at least one additional elimination rule based on the additional patient intake data, wherein the applying includes applying, by the at least one trained machine learning model, the at least one additional elimination rule to the collection to generate the subset of candidate human medical diagnoses from among the collection.

6. The computer-implemented method of claim 1, wherein the patient intake data is elicited from the patient with a virtual assistant that converses with the patient and verbally asks the patient questions relating to one or more physical symptoms and to a family medical history of the patient.

7. The computer-implemented method of claim 1, wherein the patient intake data is obtained by one or more of:

a microphone that captures sounds generated by the patient;

a visual camera that captures images of the patient;

a thermometer that measures a body temperature of the patient;

a blood pressure meter that measures a blood pressure of the patient;

an oximeter that measures an oxygen concentration in blood of the patient; and a pulse meter that measures a heart rate of the patient.

8. The computer-implemented method of claim 1, further comprising:

outputting, by at least one trained machine learning model and based on the patient intake data, a recommendation to deprescribe a medication.

9. A computer-implemented method for generating a diagnosis of a human disease of a patient, comprising:

receiving unstructured data, including medical journals;

cleaning the unstructured data to generate cleaned data;

converting the cleaned data into a standardized format, the standardized format including a table having rows and columns;

training a plurality of machine learning models using the table to generate a plurality of trained machine learning models;

receiving, via an input device, patient intake data;

determining that a first subset of the patient intake data relates to one or more physical symptoms of the patient;

determining that a second subset of the patient intake data relates to a predisposition of the patient to each of a plurality of diseases independently of the one or more physical symptoms;

providing the first subset of the patient intake data and the second subset of the patient intake data as inputs to the plurality of trained machine learning models, including:

a risk model that receives, as risk input, the second subset of the patient intake data and generates, as risk output, the predisposition of the patient to the one or more diseases; and a diagnosis model that receives, as diagnosis input, the first subset of data and the risk output, wherein the diagnosis model includes a Process Reward Model (PRM) combined with a Tree of Thoughts (TOT) method of reasoning including a tree, the PRM being configured to assess and score each step of a candidate diagnosis elimination process, and the TOT method being configured to navigate through a plurality of reasoning steps by adjusting a route through branches of the tree based on both prior conclusions and future assertions to identify a possible path to the diagnosis, the possible path including requesting and receiving additional patient intake data to rule out at least one candidate diagnosis;

generating, with the plurality of trained machine learning models, the diagnosis for the patient based on the first subset of the patient intake data and the second subset of the patient intake data, the generating including determining, by the diagnosis model, a plurality of elimination rules for the candidate diagnosis elimination process, wherein the plurality of elimination rules are based on the patient intake data; and outputting, by the diagnosis model, to a user interface of an output device:

the diagnosis; and an explanation for the diagnosis, the explanation including both symptom data and non-symptom risk data obtained from the patient intake data.

10. The computer-implemented method of claim 9, further comprising:

outputting, by at least one of the plurality of trained machine learning models and based on the first subset of the patient intake data and the second subset of the patient intake data, a recommendation for one or more tests to administer to the patient to confirm or rule out one or more candidate diagnoses of a differential diagnosis as a correct diagnosis for the patient.

11. The computer-implemented method of claim 10, the method further comprising:

providing, as additional input to the diagnosis model, results data of the one or more tests administered on the patient; and generating, with the diagnosis model, another differential diagnosis including only a subset of the candidate diagnoses based on the results data.

12. The computer-implemented method of claim 9, wherein the input device includes one or more of:

a microphone that captures sounds generated by the patient;

a visual camera that captures images of the patient;

a thermometer that measures a body temperature of the patient;

a blood pressure meter that measures a blood pressure of the patient;

an oximeter that measures an oxygen concentration in blood of the patient; and a pulse meter that measures a heart rate of the patient; and wherein the patient intake data is elicited from the patient with a virtual assistant that converses with the patient and verbally asks the patient questions relating to the one or more physical symptoms and to a family medical history of the patient.

13. The computer-implemented method of claim 9, further comprising:

accessing, with the diagnosis model and from at least one database, a collection of at least 7,000 candidate human medical diagnoses.

14. The computer-implemented method of claim 9, further comprising:

determining that a third subset of the patient intake data relates to one or more medication side effects, wherein at least one of the plurality of trained machine learning models compares the third subset of the patient intake data to medication data stored in a database, the medication data mapping medications to side effects of the medications and contraindications of the medications; and wherein the diagnosis is generated also based on the third subset of patient intake data and a comparison of the third subset of patient intake data to the medication data.

15. The computer-implemented method of claim 14, wherein generation of the diagnosis includes mapping the third subset of data and the second subset of data to each of a plurality of candidate diagnoses.

16. The computer-implemented method of claim 15, wherein generation of the diagnosis includes simultaneous processing, by the plurality of machine learning models, of the first subset of data and the second subset of data.

17. The computer-implemented method of claim 9, further comprising:

outputting, by at least one of the plurality of trained machine learning models, and based on the first subset of the patient intake data and the second subset of the patient intake data, a recommendation to deprescribe a medication.

* * * * *